(12) United States Patent
Parazynski et al.

(10) Patent No.: US 10,921,904 B2
(45) Date of Patent: Feb. 16, 2021

(54) DYNAMICALLY BALANCED MULTI-DEGREES-OF-FREEDOM HAND CONTROLLER

(71) Applicant: Fluidity Technologies Inc., Houston, TX (US)

(72) Inventors: Scott Edward Parazynski, Houston, TX (US); Jeffrey William Bull, Naperville, IL (US); Nicholas Michael Degnan, Redondo Beach, CA (US); Alina Mercedes Matson, Chaska, MN (US); Brandon Tran, Lumberton, NJ (US)

(73) Assignee: Fluidity Technologies Inc., Houston, TX (US)

( * ) Notice: Subject to any disclaimer, the term of this patent is extended or adjusted under 35 U.S.C. 154(b) by 0 days.

(21) Appl. No.: 16/844,393

(22) Filed: Apr. 9, 2020

(65) Prior Publication Data

US 2021/0011561 A1   Jan. 14, 2021

Related U.S. Application Data

(63) Continuation of application No. 16/268,434, filed on Feb. 5, 2019, now abandoned, which is a continuation
(Continued)

(51) Int. Cl.
*G06F 3/0346* (2013.01)
*G06F 3/01* (2006.01)
(Continued)

(52) U.S. Cl.
CPC ............ *G06F 3/0346* (2013.01); *A61B 34/70* (2016.02); *A61B 34/74* (2016.02); *B25J 9/1689* (2013.01);
(Continued)

(58) Field of Classification Search
CPC ...... G06F 3/0346; G06F 3/014; G06F 3/0338; G06F 3/038; A61B 34/70; A61B 34/74;
(Continued)

(56) References Cited

U.S. PATENT DOCUMENTS

| 3,028,126 A | 4/1962 | Holleman |
| 3,260,826 A | 7/1966 | Johnson |

(Continued)

FOREIGN PATENT DOCUMENTS

| CN | 102824746 A | 12/2012 |
| CN | 108885452 A | 11/2018 |

(Continued)

OTHER PUBLICATIONS

Office Action for U.S. Appl. No. 13/797,184, dated Mar. 2, 2015, 16 pages.
(Continued)

*Primary Examiner* — Charles V Hicks

(57) ABSTRACT

A controller is capable of controlling an asset or target in physical and/or virtual three-dimensional space using a single hand by generating control inputs in four or more degrees of freedom while also limiting cross-coupling (unintended motions). The controller includes a first control member is configured to be gripped in a user's single, second control member is disposed on or near a top end of the first member movable with at least one degree of freedom independently of the movement of the first control member, and a third control member positioned on the first member for displacement by one or more digits of the user's single hand and coupled with the second member to move in opposition to movement of the second control member.

16 Claims, 23 Drawing Sheets

Related U.S. Application Data of application No. 16/114,190, filed on Aug. 27, 2018, now Pat. No. 10,198,086, which is a continuation-in-part of application No. 15/964,064, filed on Apr. 26, 2018, now Pat. No. 10,520,973, which is a continuation-in-part of application No. 15/796,744, filed on Oct. 27, 2017, now Pat. No. 10,664,002.

(60) Provisional application No. 62/413,685, filed on Oct. 27, 2016.

(51) Int. Cl.
  *B25J 9/16*   (2006.01)
  *A61B 34/00*  (2016.01)
  *G06F 3/038*  (2013.01)
  *G05G 9/047*  (2006.01)
  *G06F 3/0338*  (2013.01)

(52) U.S. Cl.
  CPC ......... *G05G 9/04737* (2013.01); *G06F 3/014* (2013.01); *G06F 3/038* (2013.01); *G06F 3/0338* (2013.01); *A61B 2034/742* (2016.02); *G05G 9/04792* (2013.01); *G05G 9/04796* (2013.01); *G05G 2009/04707* (2013.01); *G05G 2009/04718* (2013.01); *G05G 2009/04774* (2013.01); *G05G 2009/04777* (2013.01); *G05G 2009/04781* (2013.01)

(58) Field of Classification Search
  CPC ............. A61B 2034/742; B25J 9/1689; G05G 9/04737; G05G 9/04792; G05G 9/04796; G05G 2009/04707; G05G 2009/04718; G05G 2009/04774; G05G 2009/04777; G05G 2009/04781
  See application file for complete search history.

(56) References Cited

U.S. PATENT DOCUMENTS

| | | |
|---|---|---|
| 4,012,014 A | 3/1977 | Marshall |
| 4,216,467 A | 8/1980 | Colston |
| 4,420,808 A | 12/1983 | Diamond et al. |
| 4,584,510 A | 4/1986 | Hollow |
| 4,590,339 A | 5/1986 | Scott-Jackson et al. |
| 4,733,214 A | 3/1988 | Andresen |
| 5,042,314 A | 8/1991 | Rytter et al. |
| 5,128,671 A | 7/1992 | Thomas, Jr. |
| 5,223,776 A | 6/1993 | Radke et al. |
| 5,317,301 A | 5/1994 | DeVolpi |
| 5,459,382 A | 10/1995 | Jacobus et al. |
| 5,503,040 A | 4/1996 | Wright |
| 5,559,432 A | 9/1996 | Logue |
| 5,565,891 A | 10/1996 | Armstrong |
| D375,765 S | 11/1996 | Kawasaki |
| 5,607,158 A | 3/1997 | Chan |
| 5,643,087 A | 7/1997 | Marcus et al. |
| 5,694,153 A | 12/1997 | Aoyagi et al. |
| D389,198 S | 1/1998 | Hama |
| 5,749,577 A | 5/1998 | Couch et al. |
| 5,781,180 A | 7/1998 | Couch et al. |
| 5,831,408 A | 11/1998 | Jacobus et al. |
| 5,963,196 A | 10/1999 | Nishiumi et al. |
| H1822 H | 12/1999 | Kelley et al. |
| 6,068,554 A | 5/2000 | Tyler |
| 6,198,471 B1 | 3/2001 | Cook |
| 6,201,196 B1 | 3/2001 | Wergen |
| 6,222,525 B1 | 4/2001 | Armstrong |
| 6,429,849 B1 | 8/2002 | An et al. |
| 6,459,420 B1 | 10/2002 | Harris |
| 6,580,418 B1 | 6/2003 | Grome et al. |
| 6,597,347 B1 | 7/2003 | Yasutake |
| 6,613,997 B2 | 9/2003 | Oster et al. |
| 6,624,806 B2 | 9/2003 | Hsu |
| 6,644,141 B2 | 11/2003 | Oikarinen |
| 6,865,342 B2 | 3/2005 | Hirata et al. |
| 7,131,389 B1 | 11/2006 | Hawkes |
| 7,170,420 B2 | 1/2007 | Phifer |
| 7,548,697 B2 | 6/2009 | Hudson et al. |
| 7,575,491 B1 | 8/2009 | Martin |
| 7,793,890 B2 | 9/2010 | Scherer |
| 7,823,685 B2 | 11/2010 | Blind |
| 7,931,239 B2 | 4/2011 | Pedersen et al. |
| 8,089,225 B2 | 1/2012 | Goossen |
| 8,100,218 B2 | 1/2012 | Case et al. |
| 8,212,770 B2 | 7/2012 | Obourn et al. |
| 8,258,917 B2 | 9/2012 | Cai et al. |
| 8,276,476 B2 | 10/2012 | Diccion |
| 8,300,012 B2 | 10/2012 | Yamamoto |
| 8,344,914 B2 | 1/2013 | Yeh |
| 8,371,187 B2 | 2/2013 | Payandeh et al. |
| 8,380,402 B2 | 2/2013 | Hobenshield |
| D678,281 S | 3/2013 | Yung |
| 8,576,168 B2 | 11/2013 | Kabasawa et al. |
| 8,716,973 B1 | 5/2014 | Lammertse |
| 8,866,597 B2 | 10/2014 | Brendel |
| 8,881,616 B2 | 11/2014 | Dize et al. |
| 8,887,597 B2 | 11/2014 | Black |
| 9,501,084 B1 | 11/2016 | Bannister |
| 9,547,380 B2 | 1/2017 | Parazynski |
| 9,727,076 B2 | 8/2017 | Smith |
| 10,152,853 B2 | 12/2018 | Provancher et al. |
| 10,198,086 B2 | 2/2019 | Parazynski et al. |
| 10,222,794 B2 | 3/2019 | Deng et al. |
| 10,324,487 B2 | 6/2019 | Parazynski et al. |
| 10,324,540 B1 | 6/2019 | Parazynski |
| 10,331,232 B2 | 6/2019 | Parazynski et al. |
| 10,331,233 B2 | 6/2019 | Parazynski et al. |
| 10,481,704 B2 | 11/2019 | Parazynski et al. |
| 10,520,973 B2 | 12/2019 | Parazynski et al. |
| 10,664,002 B2 | 5/2020 | Parazynski |
| 2002/0128064 A1 | 9/2002 | Sobota |
| 2003/0006956 A1 | 1/2003 | Wu et al. |
| 2003/0058219 A1 | 3/2003 | Shaw |
| 2003/0214484 A1 | 11/2003 | Haywood |
| 2004/0083940 A1 | 5/2004 | Shelton et al. |
| 2005/0104742 A1 | 5/2005 | Phifer |
| 2005/0159850 A1 | 7/2005 | Melman |
| 2005/0277470 A1 | 12/2005 | Watanachote |
| 2006/0137931 A1 | 6/2006 | Berg et al. |
| 2006/0156848 A1 | 7/2006 | Gosselin et al. |
| 2006/0164383 A1 | 7/2006 | Machin et al. |
| 2006/0224280 A1 | 10/2006 | Flanigan et al. |
| 2006/0262000 A1 | 11/2006 | Strong |
| 2007/0080934 A1 | 4/2007 | Chen et al. |
| 2007/0156286 A1 | 7/2007 | Yamauchi |
| 2008/0063400 A1 | 3/2008 | Hudson et al. |
| 2008/0132334 A1 | 6/2008 | Nonaka et al. |
| 2008/0174550 A1 | 7/2008 | Laurila et al. |
| 2008/0278448 A1 | 11/2008 | Nilsagard et al. |
| 2009/0152782 A1 | 6/2009 | Larsen et al. |
| 2009/0179869 A1 | 7/2009 | Slotznick |
| 2009/0213073 A1 | 8/2009 | Obermeyer et al. |
| 2009/0248220 A1 | 10/2009 | Ecton et al. |
| 2010/0097309 A1 | 4/2010 | Nishida et al. |
| 2010/0302017 A1 | 12/2010 | Guglielmo |
| 2011/0148667 A1 | 6/2011 | Yeh |
| 2011/0213384 A1 | 9/2011 | Jeong |
| 2011/0219899 A1 | 9/2011 | Dize et al. |
| 2012/0187238 A1 | 7/2012 | Lam |
| 2012/0249455 A1 | 10/2012 | Nagata et al. |
| 2013/0147611 A1 | 6/2013 | Brendel |
| 2013/0178293 A1 | 7/2013 | Nakayama et al. |
| 2013/0293362 A1 | 11/2013 | Parazynski |
| 2014/0083225 A1 | 3/2014 | Downs et al. |
| 2014/0247119 A1 | 9/2014 | Robbins et al. |
| 2014/0249695 A1 | 9/2014 | Gettings et al. |
| 2015/0253801 A1 | 9/2015 | Wuisan et al. |
| 2016/0077589 A1 | 3/2016 | Chataignier et al. |
| 2016/0195939 A1 | 7/2016 | Parazynski |
| 2016/0241767 A1 | 8/2016 | Cho et al. |
| 2017/0121000 A1 | 5/2017 | Forslund et al. |
| 2017/0233983 A1 | 8/2017 | Wright |

(56) References Cited

U.S. PATENT DOCUMENTS

| | | |
|---|---|---|
| 2017/0246533 A1 | 8/2017 | LaChappell et al. |
| 2017/0269587 A1 | 9/2017 | Hong |
| 2018/0164799 A1 | 6/2018 | Hong |
| 2018/0356907 A1 | 12/2018 | Parazynski et al. |
| 2019/0025869 A1 | 1/2019 | Parazynski |
| 2019/0033987 A1 | 1/2019 | Parazynski et al. |
| 2019/0041891 A1 | 2/2019 | Parazynski et al. |
| 2019/0041894 A1 | 2/2019 | Parazynski et al. |
| 2019/0042003 A1 | 2/2019 | Parazynski et al. |
| 2019/0042004 A1 | 2/2019 | Parazynski et al. |
| 2019/0243468 A1 | 8/2019 | Parazynski et al. |
| 2020/0285326 A1 | 9/2020 | Parazynski et al. |

FOREIGN PATENT DOCUMENTS

| | | |
|---|---|---|
| GB | 2091423 A | 7/1982 |
| JP | H11-154031 | 6/1999 |

OTHER PUBLICATIONS

Office Action for U.S. Appl. No. 13/797,184, dated Oct. 16, 2015, 15 pages.
Office Action for U.S. Appl. No. 15/071,624, dated May 17, 2016, 20 pages.
Office Action for U.S. Appl. No. 15/394,490, dated Nov. 21, 2018, 10 pages.
Office Action for U.S. Appl. No. 15/796,744, dated Dec. 21, 2018, 8 pages.
Office Action for U.S. Appl. No. 15/796,744, dated Aug. 7, 2019, 21 pages.
First Office Action for Chinese Application No. 201780080619.X, dated Mar. 16, 2020, 15 pages.
International Search Report and Written Opinion for International Application No. PCT/US2017/058905, dated Feb. 23, 2018, 5 pages.
Office Action for U.S. Appl. No. 15/964,064, dated Mar. 18, 2019, 11 pages.
International Search Report and Written Opinion for International Application No. PCT/US2018/057862, dated Jan. 11, 2019, 15 pages.
Office Action for U.S. Appl. No. 16/163,561, dated Dec. 11, 2018, 13 pages.
International Search Report and Written Opinion for International Application No. PCT/US2018/057864, dated Feb. 26, 2019, 14 pages.
Office Action for U.S. Appl. No. 16/163,563, dated Dec. 12, 2018, 22 pages.
International Search Report and Written Opinion for International Application No. PCT/US2018/057865, dated Jan. 4, 2019, 10 pages.
Office Action for U.S. Appl. No. 16/163,565, dated Dec. 19, 2018, 39 pages.
International Search Report and Written Opinion for International Application No. PCT/US2018/057874, dated Jan. 10, 2019, 10 pages.
Parazynski, Scott Edward, et al., U.S. Appl. No. 13/797,184, filed Mar. 12, 2013.
Parazynski, Scott Edward, et al., U.S. Appl. No. 15/071,624, filed Mar. 16, 2016.
Parazynski, Scott Edward, et al., UU.S. Appl. No. 15/394,490, filed Dec. 29, 2016.
Parazynski, Scott Edward, U.S. Appl. No. 15/796,744, Dynamically Balanced Multi-Degrees-Of-Freedom Hand Controller, filed Oct. 27, 2017, 64 pages.
Parazynski, Scott Edward, U.S. Appl. No. 15/964,064, Dynamically Balanced Multi-Degrees-Of-Freedom Hand Controller, filed Apr. 26, 2018, 85 pages.
Parazynski, Scott Edward, et al., U.S. Appl. No. 16/114,190, filed Aug. 27, 2018.
Parazynski, Scott Edward, et al., U.S. Appl. No. 16/163,561, filed Oct. 17, 2018.
Parazynski, Scott Edward, et al., U.S. Appl. No. 16/163,563, filed Oct. 17, 2018.
Parazynski, Scott Edward, et al., U.S. Appl. No. 16/163,565, filed Oct. 17, 2018.
"Feel Your Drone With MotionPilot's Haptic Joystick", Engadget, https://www.engadget.com/2018/01/19/motionpilothaptic-drone-joystick/, dated Jan. 19, 2018.
"CES 2018: TIE Develop World's First One-Hand Drone Controller System," LiveAt PC.com, https://liveatpc.com/ces-2018-tie-develops-worlds-first-one-hand-drone-controller-system/, dated Jan. 2018.
"[Review] JJRC H37 Baby Elfie: Is it a Worthy Successor?" DronesGlobe, http://www.dronesglobe.com/review/baby-elfie/, dated Oct. 7, 2017.
"Learn How to Pilot in Less Than 2 Minutes", Wepulsit, http://www.wepulsit.com/, dated 2017.
"InnovRC Firmware v1.2", InnovRC, http://www.innovrc.de/ivrcwiki/index.php?title=Hauptseite, dated Mar. 2013.
"H.E.A.R.T.—Hall Effect Accurate Technology: A Unique 3D Technological Innovation Built Into the New Thrustmaster Joystick," Thrustmaster, http://www.thrustmastercom/press/heart-hall-effect-accurate-technology-unique-3d-technological-innovation-built-new-thrustmaste, dated Jan. 7, 2009.
Pamplona, V. F. et al., "The image-based data glove," Proceedings of the 10th Symposium on Virtual and Augmented Reality, (SVR'2008), Joao Pessoa, Brazil, 2008, 204-211.
Wilbert, J. et al., "Semi-robotic 6 degree of freedom positioning for intracranial high precision radiotherapy; first phantom and clinical results," Radiation Oncology, 5(42), 11 pages, May 26, 2010.
Zhai, X., "Human performance in six degree of freedom input control," Doctoral Dissertation University of Toronto, Graduate Department of Industrial Engineering, 179 pages, 1995.
Office Action for U.S. Appl. No. 16/682,509, dated Jul. 20, 2020, 11 pages.

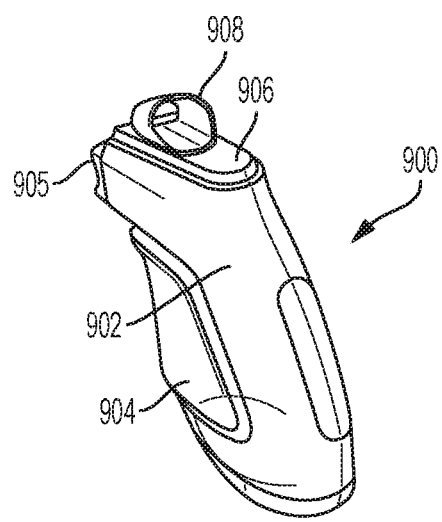 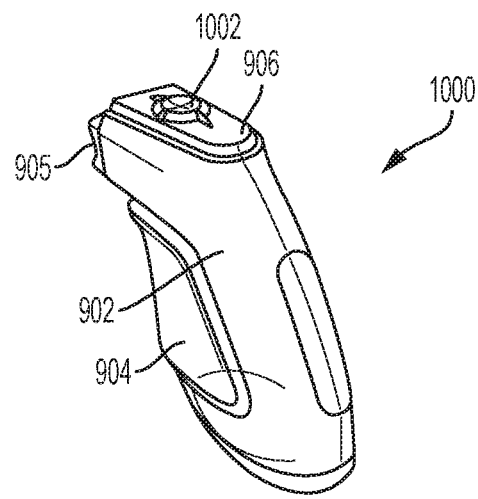
FIG. 9  FIG. 10
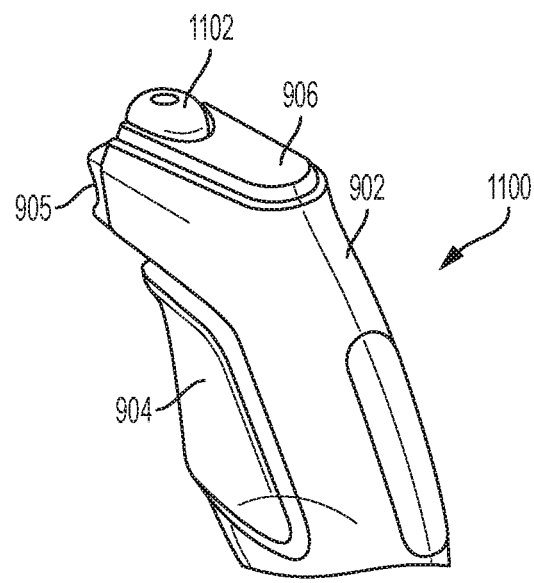
FIG. 11

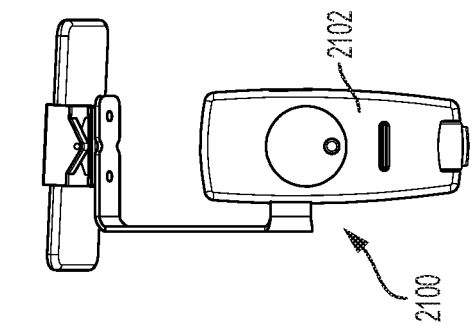
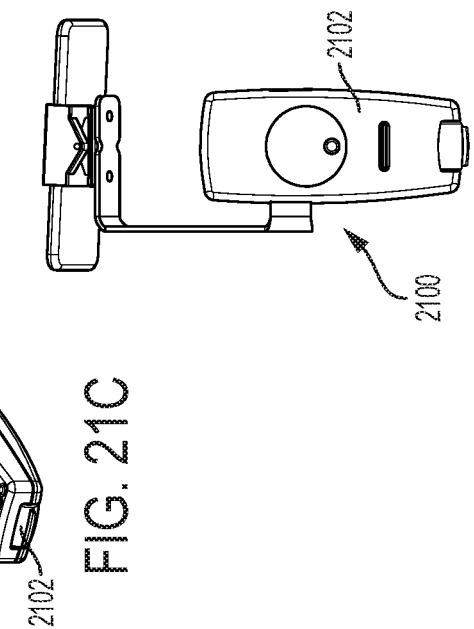
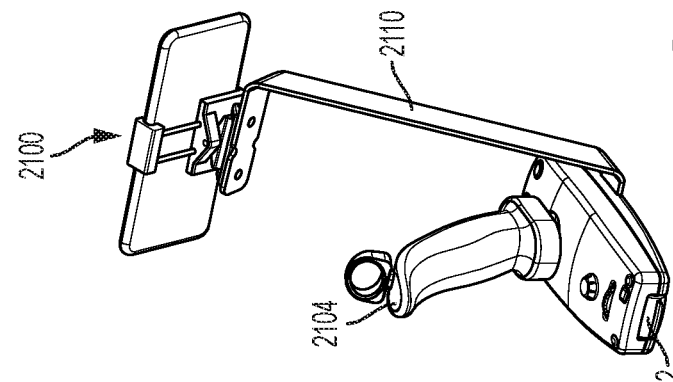
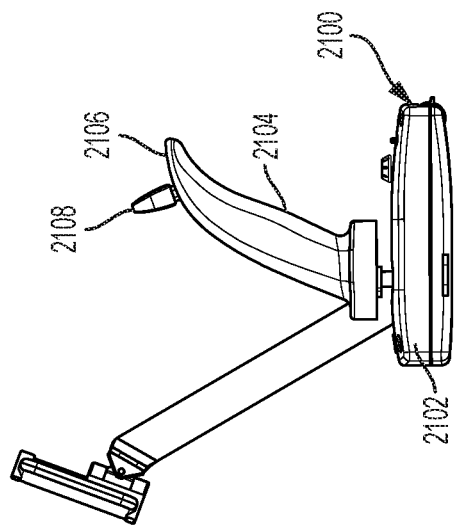
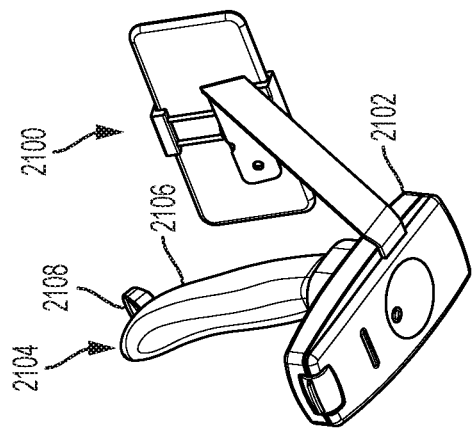
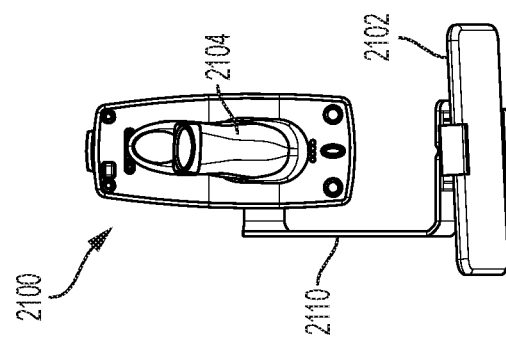

DYNAMICALLY BALANCED MULTI-DEGREES-OF-FREEDOM HAND CONTROLLER

RELATED APPLICATION

This application is a continuation of U.S. application Ser. No. 16/268,434 filed Feb. 5, 2019, which is a continuation of U.S. application Ser. No. 16/114,190 filed Aug. 27, 2018, which is a continuation-in-part of U.S. application Ser. No. 15/964,064, filed Apr. 26, 2018, which is a continuation-in-part of Ser. No. 15/796,744 filed Oct. 27, 2017, which claims the benefit of U.S. provisional patent application No. 62/413,685 filed Oct. 27, 2016. The entirety of each of these applications is incorporated herein by reference for all purposes.

FIELD OF THE INVENTION

The present disclosure relates generally to control systems and more particularly to a controller that provides a user with the ability to send command signals for up to six independent degrees of freedom, substantially limiting cross-coupling, using a controller that is operable with a single hand.

BACKGROUND OF THE INVENTION

Conventionally, multiple discrete controllers are utilized to allow a user to control a control target having more than three degrees of freedom. Furthermore, multiple discrete controllers have been required for any conventional control system that controls a control target having six degrees of freedom. For example, a set of independent controllers or input devices (e.g., joysticks, control columns, cyclic sticks, foot pedals, and/or other independent controllers as may be known by one or more of ordinary skill in the art) may be provided to receive a variety of different rotational parameters (e.g., pitch, yaw, and roll) from a user for a control target (e.g., an aircraft, submersible vehicles, spacecraft, a control target in a virtual environment, and/or a variety of other control targets as may be known by one or more of ordinary skill in the art). Similarly, a set of independent controllers may be provided to control other navigational parameters such as translation (e.g., x-, y-, and z-axis movement) in a three-dimensional (3D) space, velocity, acceleration, and/or a variety of other command parameters.

U.S. patent application Ser. Nos. 13/797,184 and 15/071,624, respectively filed on Mar. 12, 2013, and Mar. 16, 2016, which are both incorporated herein by reference in their entireties, describe several embodiments of a control system that allows a user to control a control target in up to six degrees of freedom (6-DoF) simultaneously and independently, using a single controller. In one embodiment, a unified hand controller may include a first control member for receiving rotational inputs (e.g., pitch, yaw, and roll) and a second control member that extends from the first control member for receiving translational inputs (e.g., displacement along X, Y, and Z axes) from the user. The first control member and the second control member on the unified hand controller may be positioned by a user using a single hand to control the control target in up to 6-DoF.

SUMMARY

Previously known drone, virtual reality, augmented reality, computer and gaming input devices are not intuitive, require substantial initial and proficiency training, and are operated with two hands. They are also typically not mobile.

Various aspects of the single-handed controllers described below, individually and/or in combination with other of these aspects, offer several improvements that better enable users, whether they are in motion or at rest (such as a computer augmented or virtual reality gamers, pilots, hikers, skiers, security/SAR personnel, war-fighters, and others, for example) to control an asset or target in physical and/or virtual three-dimensional space, by enabling generation of control inputs while also limiting cross-coupling (unintended motions). A controller with these features can be used to allow the controller to decouple translation from attitude adjustments in the control requirements of computer aided design, drone flight, various types of computer games, virtual and augmented reality and other virtual and physical tasks where precise movement through space is required.

According to one aspect of the disclosure, a hand controller includes first, second, and third control members. The first control member is movable with at least two degrees of freedom and generates in response a first set of independent control inputs. Movement or displacement of the first member may be sensed, and a control input generated, for each degree of freedom using one or more sensors, each of which is capable of detecting and, if desired, measuring displacement in one or more of the degrees of freedom of displacement. The first control member is configured to be gripped in a user's single hand by the user placing it in the palm of the hand and wrapping at least several of their fingers at least partially around the body of the first member to hold it. The second control member is disposed on or near a top end of the first member, near where the thumb or index finger of a hand might rest when the first member is gripped. In one embodiment it is movable with at least one degree of freedom and in other embodiments two or three degrees of freedom independently of the movement of the first control member. In response to its independent movement, movement of the second control member results in a second set of control inputs, one for each degree of freedom in which it can be displaced. The control inputs of the second set are independent of the control inputs of the first set.

Extended operation of a controller with a second member with a digit for independent control inputs, particularly when the second member is pulled up or pushed down by the thumb, might lead to fatigue. A third control member is positioned on the first member for displacement by one or more digits of the user's single hand and coupled with the second member to move in opposition to movement of the second control member in one of the degrees of freedom of movement of the second control member, for example in the one in which a user's thumb pulls up to displace the second control member. The third control member is mounted on the first member in a position for enabling one or more digits on a user's hand that are not being used to displace the second control member to squeeze the third member and cause its displacement. The third member is coupled to the second member to displace the second member when the third member is displaced inwardly by the user squeezing or pulling the third member with one or more fingers. Pushing down the second control member may, if desired, also push outwardly from the controller the third control member, allowing user's thumb or index finger to be dynamically balanced by the user's other digits.

In a separate aspect of the disclosure, a hand controller having at least first and second control members (and, optionally, a third control member), which is configured for gripping by a user's single hand, may be coupled with a wrist or forearm brace that serves as a reference for rotational axes, particularly yaw. Yaw is difficult to measure with an inertial measurement unit (IMU) within a hand-held controller. For example, although an IMU in the hand controller might be able to sense and measure with sufficient precision and sensitivity pitch and roll (rotation about the X and Y axes) of the first member, outputs of an IMU for rotation about the Z-axis corresponding to yaw of the first control member can be noisy. In one embodiment, a sensor measures displacement of a linkage between the first control member and a user's wrist or forearm caused by the user bending the user's wrist to rotate the controller to indicate yaw.

As illustrated by several representative embodiments described below, a single-handed controller mounts on the wrist and registers displacement from a neutral position defined relative to the wrist, allowing flight, gaming or augmented reality motion control in up to six degrees of freedom of motion (6-DoF) with precision. Passive mechanical, vibration haptic or active mechanical feedback may inform the user of their displacement from zero in each of these 6-DoF. With such a single-handed control, movement through the air like a fighter pilot with intuitive (non-deliberate cognitive) inputs is possible.

In accordance with another aspect of the disclosure, a forearm brace coupled with a controller can used in combination with an index finger loop to open or close a grasp on an object in a virtual world.

Another aspect of different ones of the representative embodiments of hand controllers described below, involves a two-handed controller that provides a consistent, known reference frame stabilized by the non-dominant hand even while moving, e.g., walking, skiing, running, driving. One, optional, embodiment of the hand controller can be plugged into the surface of a base, allowing the non-flying hand to stabilize the base as it is being flown.

Moving a point of reference (POR) through physical or virtual space by way of a hand controller raises the problem of requiring insight into displacement in every degree of freedom being controlled so that the location of the "zero input" is known for each degree of freedom independently and at the same time. For example, for drones, the zero input positions for x, y, and z axes and yaw need to be always known. Other flight regimes, such as virtual and augmented reality, computer gaming and surgical robotics may require as many as six independent degrees of freedom simultaneously (movement along x, y, and z axes, and pitch, yaw, and roll). Moreover, for drone flight and virtual and augmented reality systems in particular, the ability to be mobile while maintaining precise control of the point of reference is desirable.

In one of the representative embodiments, a first control member in the form of a joystick mounted to a base allows for pitch, yaw and roll inputs where it connects to the base, with centering mechanisms to generate forces to inform a user of zero command by tactile feel. A second control member on top of the joystick, in a position that can displaced with a thumb or another digit along one or more of the X, Y and Z axes with respect to the first control member generates control signals in up to 3 additional degrees of freedom, also with tactile feedback of zero command. For example, magnetic or mechanical detents can be used to define a center or "zero" input for each of the multiple degrees of freedom of one or more of the controllers and cause the user feels a slight increase in force as the controller member departs from the center or "zero input" position. When re-entering the center of the range of travel of a controller member along one of the degrees of freedom of movement, a slight change in force is felt as "zero input" is restored. These detent forces can be felt in the user's hands, simultaneously and independently for each degree of freedom being commanded.

Additional aspects, advantages, features and embodiments are described below in conjunction with the accompanying drawings. All patents, patent applications, articles, other publications, documents and things referenced herein are hereby incorporated herein by this reference in their entirety for all purposes. To the extent of any inconsistency or conflict in the definition or use of terms between any of the incorporated publications, documents or things and the present application, those of the present application prevail.

BRIEF DESCRIPTION OF THE DRAWINGS

For promoting an understanding of the principles of the invention that is claimed below, reference will now be made to the embodiments, or examples, illustrated in the appended drawings. It will be understood that, by describing specific embodiments and examples, no limitation of the scope of the invention, beyond the literal terms set out in the claims, is intended. Alterations and further modifications to the described embodiments and examples are possible while making use of the claimed subject matter, and therefore are contemplated as being within the scope of the invention as claimed.

FIG. 9 illustrates a perspective view of a third, representative embodiment of a controller having a secondary control member in the form of a thumb loop.

FIG. 10 illustrates a perspective view of a fourth, representative embodiment of a controller having a gantry-type secondary control member.

FIG. 11 illustrates a perspective view of a fifth, representative embodiment of a controller having a trackball-type secondary control member.

FIGS. 21A-21F illustrate a controller, according to an embodiment.

DESCRIPTION OF ILLUSTRATIVE EMBODIMENTS

Figure 1:
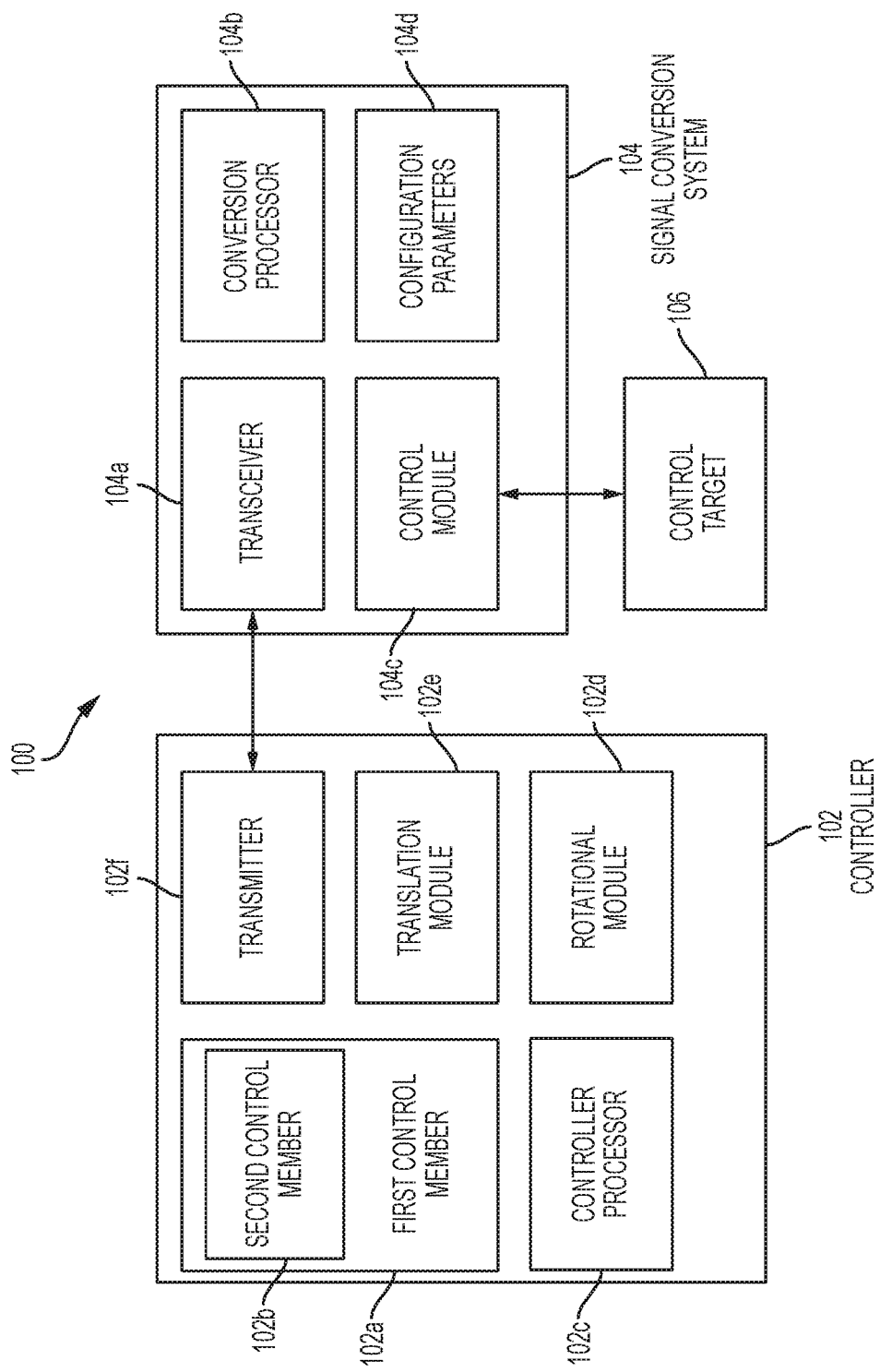
FIG. 1 is a schematic view of an embodiment of a control system.

In the drawings and description that follows, the drawings are not necessarily to scale. Certain features of the invention may be shown exaggerated in scale or in schematic form. Details or presence of conventional or previously described elements may not be shown in the interest of clarity and conciseness.

The controller of the present disclosure can be embodied in several forms while still providing at least one advantage mentioned below. Many of the specific examples described below offer multiple advantages. Specific embodiments are described in detail and are shown in the drawings, with the understanding that the present disclosure is to be considered an exemplification of the principles of the invention and is not intended to limit the invention to that illustrated and described herein. It is to be fully recognized that the different teachings of the embodiments discussed below may be employed separately or in any suitable combination to produce desired results. The various characteristics mentioned above, as well as other features and characteristics described in more detail below, will be readily apparent to those skilled in the art upon reading the following description of illustrative embodiments of the invention, and by referring to the drawings that accompany the specification.

The present disclosure describes several embodiments of a control system that allows a user to control a control target or point of reference (POR) in up to six degrees of freedom (6-DoF) using a single controller. In one embodiment, a unified hand controller may include a first control member for receiving a first set of one, two or three inputs from a user and a second control member that extends from the first control member that can receive a second set of one, two or three additional inputs from the user. The user inputs are generated by the user displacing each control members in up to three degrees of freedom. These controller maps user inputs to preselected outputs that are used to control a target control system. The first control member and the second control member on the unified hand controller may be repositioned by a user using a single hand to control the control target in up to six degrees of freedom.

More specifically, in some of the embodiments of a control system described below, a user is able to control a control target in 6-DoF using a single controller. In one embodiment, a unified hand controller may include a first control member for receiving rotational inputs (e.g., pitch, yaw, and roll) and a second control member that extends from the first control member and that is for receiving translational inputs (e.g., movement along x, y, and z axes). Alternately, the user might program these control system inputs to different coordinate frames as desired or necessary for the operation being performed. As described in further detail below, the first control member and the second control member on the unified hand controller may be repositioned by a user using a single hand to control the control target in 6-DoF.

The embodiments described below are examples of an improved single-hand controller with one or more additional features as compared to prior art hand controllers. These additional features and enhancements include: improved Z-axis spring forces and self-centering/zeroing capability for a second member that is controlled by a user's thumb when gripping a first member of a controller; a larger gantry on top of first member for moving the second member in along X and Y axes; a replaceable or resizable thumb loop for the second control member; a forearm or wrist stabilization for ambulatory use (potentiometers, Hall effect sensors, or optical encoders for translations along X, Y and Z axes, such as for use in drone applications and for integrating with virtual/augmented reality); a mouse-based implementation for improved CAD object manipulation; and combinations of any two or more of the preceding features.

The hand controller with any one or more of these features, and their variations, can be used in applications such as flight simulation, computer aided design (CAD), drone flight, fixed wing and rotary wing flight, computer gaming, virtual and augmented reality navigation, aerial refueling, surgical robotics, terrestrial and marine robotic control, and many others, some of which are described below.

Referring initially to FIG. 1, a control system 100 for controlling a control target in 6-DoF. The control system 100 includes a controller 102 that is coupled to a signal conversion system 104 that is further coupled to a control target 106. In an embodiment, the control target 106 may include end effectors (e.g., the end of a robotic forceps, a robotic arm end effector with snares), camera field-of-views (e.g., including a camera center field-of-view and zoom), vehicle velocity vectors, etc. While the controller 102 and the signal conversion system 104 are illustrated separately, one of ordinary skill in the art will recognize that some or all of the controller 102 and the signal conversion system 104 may be combined without departing from the scope of the present disclosure.

The controller 102 includes a first control member 102a and a second control member 102b that is located on the first control member 102a. In some embodiments, the controller 102 may further include a third control member (not shown) also located on the first control member 102a. In this description, controller 102 is intended to be representative of the all of the controllers described herein, unless otherwise indicated. A controller processor 102c is coupled to each of the first control member 102a and the second control member 102b. In an embodiment, the controller processor 102c may be a central processing unit, a programmable logic controller, and/or a variety of other processors as may be known by one or more of ordinary skill in the art. The controller processor 102c is also coupled to each of a rotational module 102d, a translation module 102e, and a transmitter 102f. While not illustrated or described in any further detail, other connections and coupling may exist between the first control member 102a, the second control member 102b, the controller processor 102c, the rotation module 102d, the translation module 102e, and the transmitter 102f while remaining within the scope of the present disclosure. Furthermore, components of the controller may be combined or substituted with other components as may be known by one or more of ordinary skill in the art while remaining with the scope of the present disclosure.

The signal conversion system 104 in the control system 100 includes a transceiver 104a that may couple to the transmitter 102f in the controller 102 through a wired connection, a wireless connection, and/or a variety of other connections as may be known by one or more of ordinary skill in the art. A conversion processor 104b is coupled to the transceiver 104a, a control module 104c, and configuration parameters 104d that may be included on a memory, a storage device, and/or other computer-readable mediums as may be known by one or more of ordinary skill in the art. In an embodiment, the conversion processor 104b may be a central processing unit, a programmable logic controller, and/or a variety of other processors known to those of ordinary skill in the art. While not illustrated or described in any further detail, other connections and coupling may exist between the transceiver 104a, the conversion processor 104b, the control module 104c, and the configuration parameters 104d while remaining within the scope of the present disclosure. Furthermore, components of the signal conversion system 104 may be combined or substituted with other components as may be known by one or more of ordinary skill in the art while remaining with the scope of the present disclosure. The control module 104c may be coupled to the control target 106 through a wired connection, a wireless connection, and/or a variety of other connections as may be known by one or more of ordinary skill in the art.

In an embodiment, the controller 102 is configured to receive input from a user through the first control member 102a and/or the second control member 102b and transmit a signal based on the input. For example, the controller 102 may be provided as a "joystick" for navigating in a virtual environment (e.g., in a video game, on a real-world simulator, as part of a remote control virtual/real-world control system, and/or in a variety of other virtual environments as may be known by one or more of ordinary skill in the art.) In another example, the controller 102 may be provided as a control stick for controlling a vehicle (e.g., an aircraft, a submersible, a spacecraft, and/or a variety of other vehicles as may be known by one or more of ordinary skill in the art). In another example, the controller 102 may be provided as a control stick for controlling a robot or other non-vehicle device (e.g., a surgical device, an assembly device, and/or variety of other non-vehicle devices known to one of ordinary skill in the art).

In the embodiment discussed in further detail below, the controller 102 includes a control stick as the first control member 102a that is configured to be repositioned by the user. The repositioning of the control stick's first control member 102a allows the user to provide rotational inputs using the first control member 102a that include pitch inputs, yaw inputs, and roll inputs, and causes the controller processor 102c to output rotational movement output signals including pitch movement output signals, a yaw movement output signals, and roll movement output signals. In particular, tilting the control stick first control member 102a forward and backward may provide the pitch input that produces the pitch movement output signal, rotating the control stick first control member 102a left and right about its longitudinal axis may provide the yaw input that produces the yaw movement output signal, and tilting the control stick first control member 102a side to side may provide the roll input that produces the roll movement output signal. As discussed below, the movement output signals that result from the repositioning of the first control member 102a may be reconfigured from that discussed above such that similar movements of the first control member 102a to those discussed above result in different inputs and movement output signals (e.g., tilting the control stick first control member 102a side to side may be configured to provide the yaw input that produces the yaw movement output signal while rotating the control stick first control member 102a about its longitudinal axis may be configured provide the roll input that produces the roll movement output signal.)

Rotational inputs using the control stick first control member 102a may be detected and/or measured using the rotational module 102d. For example, the rotational module 102d may include displacement detectors for detecting the displacement of the control stick first control member 102a from a starting position as one or more of the pitch inputs, yaw inputs, and roll inputs discussed above. Displacement detectors may include photo detectors for detecting light beams, rotary and/or linear potentiometers, inductively coupled coils (Hall effect sensors), physical actuators, gyroscopes, switches, transducers, and/or a variety of other displacement detectors as may be known by one or more of ordinary skill in the art. In some embodiments, the rotational module 102*d* may include accelerometers for detecting the displacement of the control stick first control member 102*a* from a starting position in space. For example, the accelerometers may each measure the proper acceleration of the control stick first control member 102*a* with respect to an inertial frame of reference.

In other embodiments, inputs using the control stick first control member 102*a* may be detected and/or measured using breakout switches, transducers, and/or direct switches for each of the three ranges of motion (e.g., front to back, side to side, and rotation about a longitudinal axis) of the control stick first control member 102*a*. For example, breakout switches may be used to detect when the control stick first control member 102*a* is initially moved (e.g., 2°) from a null position for each range of rotation, transducers may provide a signal that is proportional to the displacement of the control stick first control member 102*a* for each range of motion, and direct switches may detect when the control stick first control member 102*a* is further moved (e.g., 12°) from the null position for each range of motion. The breakout switches and direct switches may also allow for acceleration of the control stick first control member 102*a* to be detected. In an embodiment, redundant detectors and/or switches may be provided in the controller 102 to ensure that the control system 100 is fault tolerant.

In the embodiment discussed in further detail below, the second control member 102*b* extends from a top, distal portion of the control stick first control member 102*a* and is configured to be repositioned by the user independently from and relative to the control stick first control member 102*a*. The repositioning of the second control member 102*b* discussed below allows the user to provide translational inputs using the second control member 102*b* that include x-axis inputs, y-axis inputs, and z-axis inputs, and causes the control processor 102*c* to output a translational movement output signals including x-axis movement output signals, y-axis movement output signals, and z-axis movement output signals. For example, tilting the second control member 102*b* forward and backward may provide the x-axis input that produces the x-axis movement output signal, tilting the second control member 102*b* side to side may provide the y-axis input that produces the y-axis movement output signal, and moving the second control member 102*b* up and down may provide the z-axis input that produces the z-axis movement output signal. As discussed below, the signals that result from the repositioning of the second control member 102*b* may be reconfigured from that discussed above such that similar movements of the second control member 102*b* to those discussed above result in different inputs and movement output signals (e.g., tilting the second control member 102*b* forward and backward may be configured to provide the z-axis input that produces the z-axis movement output signal while moving the second control member 102*b* up and down may be configured to provide the x-axis input that produces the x-axis movement output signal.) In an embodiment, the second control member 102*b* is configured to be repositioned solely by a thumb of the user while the user is gripping the control stick first control member 102*a* with the hand that includes that thumb.

Translational inputs using the second control member 102*b* may be detected and/or measured using the translation module 102*e*. For example, the translation module 102*e* may include translational detectors for detecting the displacement of the second control member 102*b* from a starting position as one or more of the x-axis inputs, y-axis inputs, and z-axis inputs discussed above. Translation detectors may include physical actuators, translational accelerometers, and/or a variety of other translation detectors as may be known by one or more of ordinary skill in the art (e.g., many of the detectors and switches discussed above for detecting and/or measuring rotational input may be repurposed for detecting and/or measuring translation input.)

It should be appreciated, that the first control member 102*a* is not limited to rotational inputs nor is the second control member 102*b* limited to translational inputs. For example, the first control member 102*a* may correspond to translational inputs while the second control member 102*b* corresponds to rotational inputs. In some embodiments, the input associated with a respective rotational or translational movement may be based on user preference.

In an embodiment, the controller processor 102*c* of the controller 102 is configured to generate control signals to be transmitted by the transmitter 102*f*. As discussed above, the controller processor 102*c* may be configured to generate a control signal based on one or more rotational inputs detected and/or measured by the rotational module 102*d* and/or one or more translational inputs detected and/or measured by the translation module 102*e*. Those control signal generated by the controller processor 102*c* may include parameters defining movement output signals for one or more of 6-DoF (i.e., pitch, yaw, roll, movement along an x-axis, movement along a y-axis, movement along a z-axis). In several embodiments, a discrete control signal type (e.g., yaw output signals, pitch output signals, roll output signals, x-axis movement output signals, y-axis movement output signals, and z-axis movement output signals) is produced for each discrete predefined movement (e.g., first control member 102*a* movement for providing pitch input, first control member 102*a* movement for providing yaw input, first control member 102*a* movement for providing roll input, second control member 102*b* movement for providing x-axis input, second control member 102*b* movement for providing y-axis input, and second control member 102*b* movement for providing z-axis input) that produces that discrete control signal. Beyond 6-DoF control, discrete features such as ON/OFF, trim, and other multi-function commands may be transmitted to the control target. Conversely, data or feedback may be received on the controller 102 (e.g., an indicator such as an LED may be illuminated green to indicate the controller 102 is on.)

In an embodiment, the transmitter 102*f* of the controller 102 is configured to transmit the control signal through a wired or wireless connection. For example, the control signal may be one or more of a radio frequency ("RF") signal, an infrared ("IR") signal, a visible light signal, and/or a variety of other control signals as may be known by one or more of ordinary skill in the art. In some embodiments, the transmitter 102*f* may be a BLUETOOTH® transmitter configured to transmit the control signal as an RF signal according to the BLUETOOTH® protocol (BLUETOOTH® is a registered trademark of the Bluetooth Special Interest Group, a privately held, not-for-profit trade association headquartered in Kirkland, Wash., USA).

In an embodiment, the transceiver 104*a* of the signal conversion system 104 is configured to receive the control signal transmitted by the transmitter 102*f* of the controller 102 through a wired or wireless connection, discussed above, and provide the received control signal to the conversion processor 104*b* of the signal conversion system 104.

In an embodiment, the conversion processor 104*b* is configured to process the control signals received from the controller 102. For example, the conversion processor 104*b* may be coupled to a computer-readable medium including instructions that, when executed by the conversion processor 104b, cause the conversion processor 104b to provide a control program that is configured to convert the control signal into movement commands and use the control module 104c of the signal conversion system 104 to control the control target 106 according to the movement commands. In an embodiment, the conversion processor 104b may convert the control signal into movement commands for a virtual three-dimensional ("3D") environment (e.g., a virtual representation of surgical patient, a video game, a simulator, and/or a variety of other virtual 3D environments as may be known by one or more of ordinary skill in the art.). Thus, the control target 106 may exist in a virtual space, and the user may be provided a point of view or a virtual representation of the virtual environment from a point of view inside the control target (i.e., the control system 100 may include a display that provides the user a point of view from the control target in the virtual environment). In another example, the control target 106 may be a physical device such as a robot, an end effector, a surgical tool, a lifting system, etc., and/or a variety of steerable mechanical devices, including, without limitation, vehicles such as unmanned or remotely-piloted vehicles (e.g., "drones"); manned, unmanned, or remotely-piloted vehicles and landcraft; manned, unmanned, or remotely-piloted aircraft; manned, unmanned, or remotely-piloted watercraft; manned, unmanned, or remotely-piloted submersibles; as well as manned, unmanned, or remotely-piloted space vehicles, rocketry, satellites, and such like.

In an embodiment, the control module 104c of the signal conversion system 104 is configured to control movement of the control target 106 based on the movement commands provided from the control program in signal conversion system 104. In some embodiments, if the control target 106 is in a virtual environment, the control module 104c may include an application programming interface (API) for moving a virtual representation or point of view within the virtual environment. API's may also provide the control module 104c with feedback from the virtual environment such as, for example, collision feedback. In some embodiments, feedback from the control target 106 may allow the control module 104c to automatically adjust the movement of the control target to, for example, avoid a collision with a designated region (e.g., objects in a real or virtual environment, critical regions of a real or virtual patient, etc.). In other embodiments, if the control target 106 is a physical device, the control module 104c may include one or more controllers for controlling the movement of the physical device. For example, the signal conversion system 104 may be installed on-board a vehicle, and the control module 104c may include a variety of physical controllers for controlling various propulsion and/or steering mechanisms of the vehicle.

In an embodiment, the signal conversion system 104 includes configuration parameters 104d for use by the conversion processor 104b when generating movement commands using the signals from the controller 102. Operating parameters may include, but are not limited to, gains (i.e., sensitivity), rates of onset (i.e., lag), deadbands (i.e., neutral), limits (i.e., maximum angular displacement), and/or a variety of other operating parameters as may be known by one or more of ordinary skill in the art. In an embodiment, the gains of the first control member 102a and the second control member 102b may be independently defined by a user. In this example, the second control member 102b may have increased sensitivity compared to the control stick first control member 102a to compensate, for example, for the second control member 102b having a smaller range of motion that the control stick's first control member 102a. Similarly, the rates of onset for the first control member 102a and the second control member 102b may be defined independently to determine the amount of time that should pass (i.e., lag) before a repositioning of the first control member 102a and the second control member 102b should be converted to actual movement of the control target 106. The limits and deadbands of the first control member 102a and the second control member 102b may be independently defined as well by calibrating the neutral and maximal positions of each.

In an embodiment, operating parameters may also define how signals sent from the controller 102 in response to the different movements of the first control member 102a and the second control member 102b are translated into movement commands that are sent to the control target. As discussed above, particular movements of the first control member 102a may produce pitch, yaw, and roll rotational movement output signals, while particular movements of the second control member 102b may produce x-axis, y-axis, and z-axis translational movement output signals. In an embodiment, the operating parameters may define which movement commands are sent to the control target 106 in response to movements and resulting movement output signals from the first control member 102a and second control member 102b.

A single hand controller like the ones described shown in FIGS. 7-20B, can provide up to 6 degrees of freedom control. For applications in many types of physical and virtual 3-D environments, all 6 degrees of freedom may be required, such as moving a spacecraft or many types of aircraft, or certain computer games and virtual reality and augmented reality environments. In many of these cases, the best way to manage them is to map the x-axis, y-axis, and z-axis translational output signals generated by displacement of the second control member to x-axis, y-axis and z-axis movements in the target application, and use the pitch, roll and yaw rotational output signals generated by displacement of the first control member to provide rotational control output signals that control pitch, roll and yaw in the target application.

However, for many other applications like drone flight, when only 4 command axes are needed, a user's inputs might be split in different ways, depending whether the hand controller is mounted on a fixed base for the controller, stabilized by the non-dominant hand, or coupled with a forearm brace. For example, when using a forearm brace to support the hand controller and provide a frame of reference, it might be more desirable to control the y-axis movement of the drone using the second member but use the first control member to control x-axis movement and yaw. Because the controller's individual input "devices" are easily programmable, the user has the ability to choose whatever combination of inputs and axes the user would like.

In some embodiments, the configuration parameters 104d may be received from an external computing device (not shown) operated by the user. For example, the external computing device may be preconfigured with software for interfacing with the controller 102 and/or the signal conversion system 104. In other embodiments, the configuration parameters 104d may be input directly by a user using a display screen included with the controller 102 or the signal conversion system 104. For example, the first control member 102a and/or second control member 102b may be used to navigate a configuration menu for defining the configuration parameters 104d.

Figure 2:
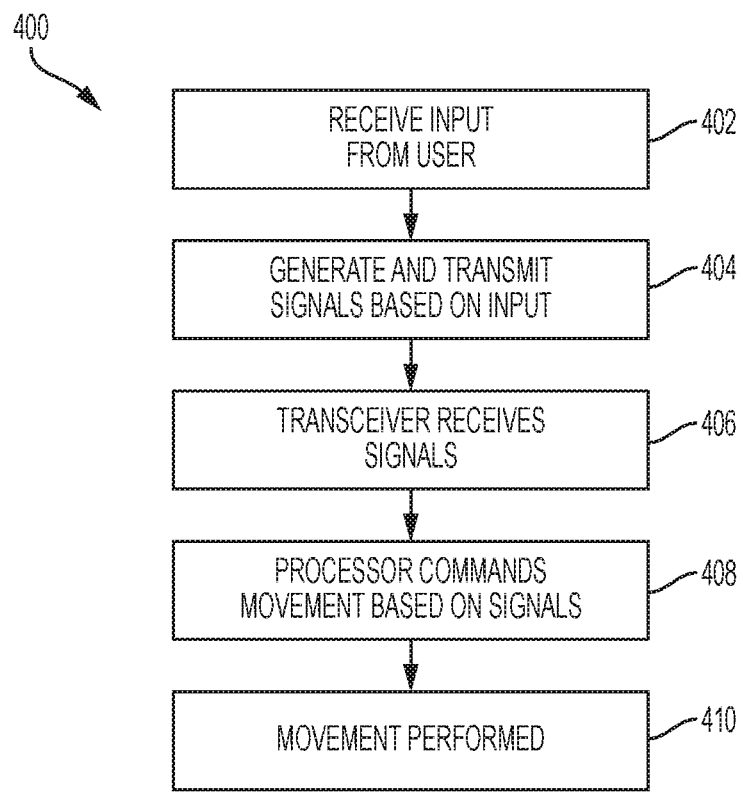
FIG. 2 is a flowchart illustrating an embodiment of a method for controlling a control target.
Figure 3A:
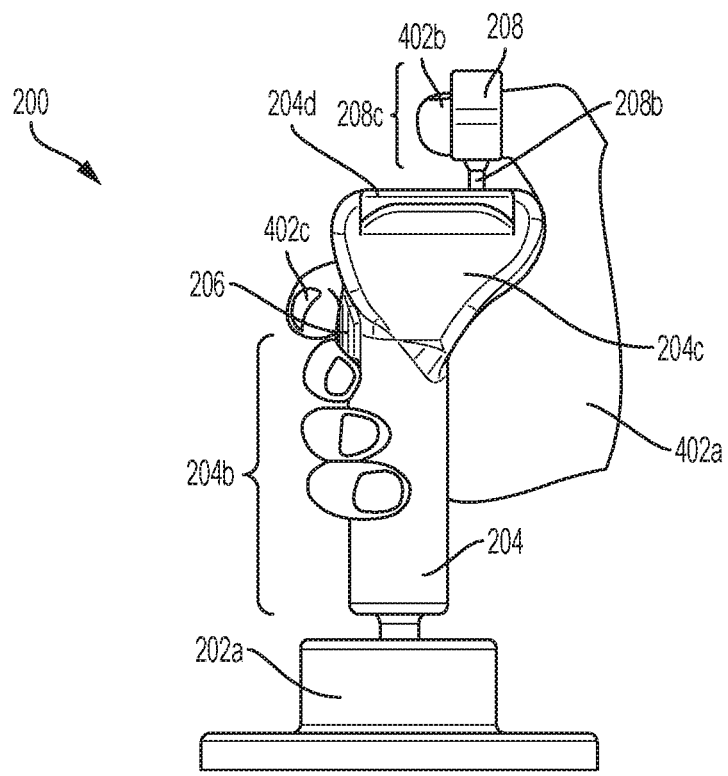
FIG. 3A is a side view illustrating an embodiment of a user using a controller with a single hand.
Figure 3B:
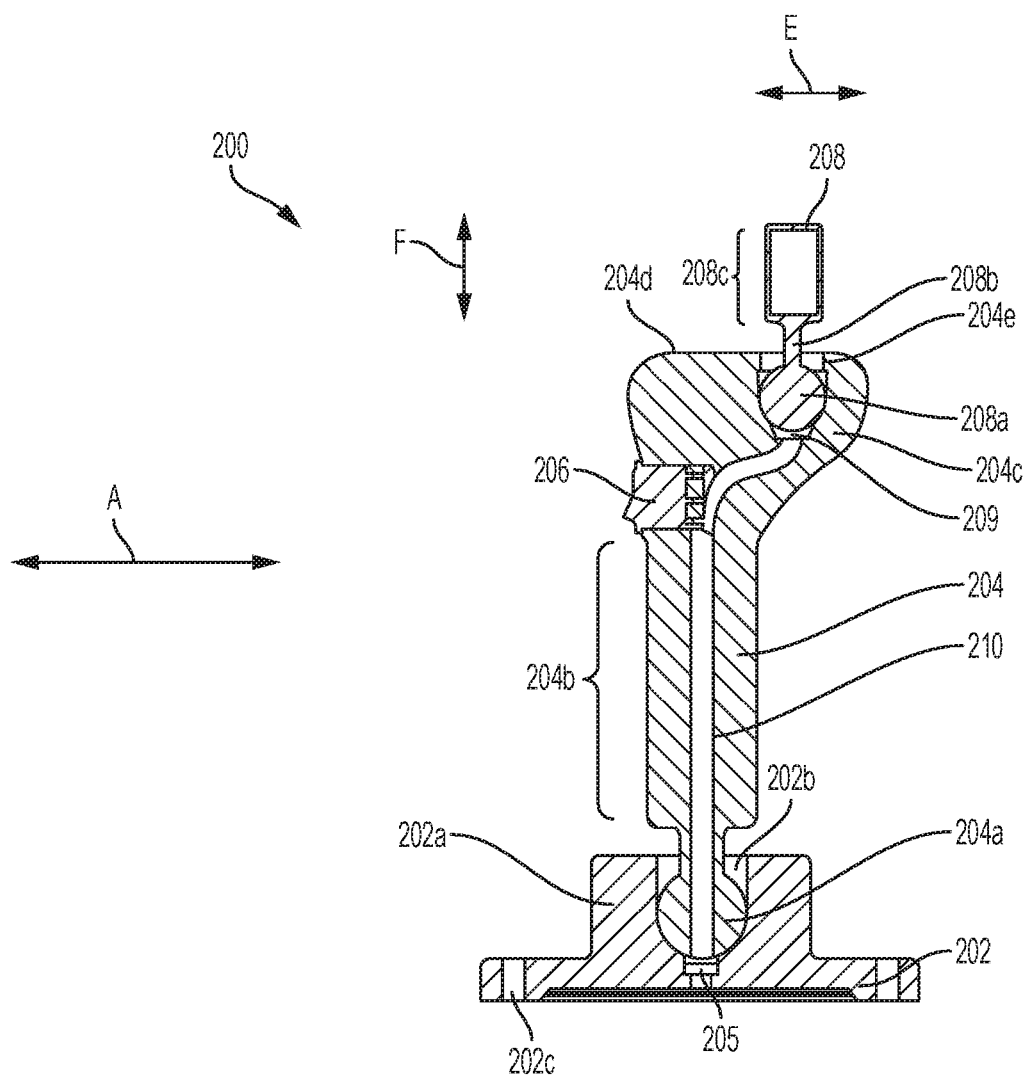
FIG. 3B is a cross-sectional view of the embodiment depicted in FIG. 3A.
Figure 3C:
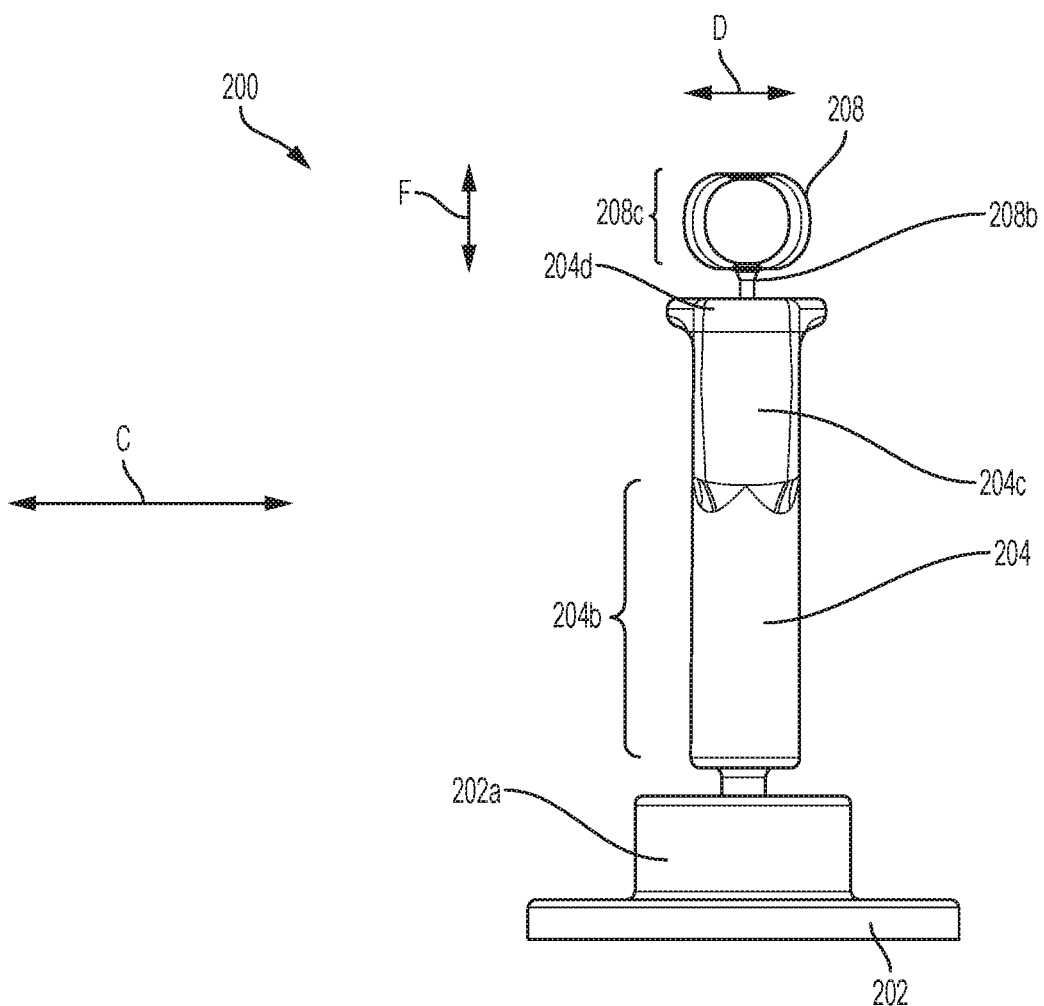
FIG. 3C is a front view of the embodiment depicted in FIG. 3A.

Referring now to FIGS. 2 and 3A-C, a method 400 for controlling a control target is illustrated using one of as single hand controller. The illustrated controller in FIGS. 3A-C is representative of single hand controllers having a first control member gripped by a user's hand, which can be displaced to generate a first set of control outputs and a second control member that is positioned on the first control member, to be manipulated by the thumb on the hand gripping the first control member, to generate a second set of control outputs. Any of the single hand controllers described herein may be used with the methods described in connection with these figures, unless otherwise specifically stated. As is the case with the other methods described herein, various embodiments may not include all of the steps described below, may include additional steps, and may sequence the steps differently. Accordingly, the specific arrangement of steps shown in FIG. 2 should not be construed as limiting the scope of controlling the movement of a control target.

The method 400 begins at block 402 where an input is received from a user. As previously discussed, a user may grasp the first control member with a hand, while using a thumb on a second control member. As illustrated in FIGS. 3A-C, a user may grasp the first control member 204 with a hand 402a, while extending a thumb 402b through the thumb channel defined by the second control member 208. Furthermore, the user may position a finger 402c over the control button 206. One of ordinary skill in the art will recognize that while a specific embodiment having the second control member 208 positioned for thumb actuation and control button 206 for finger actuation are illustrated, other embodiments that include repositioning of the second control member 208 (e.g., for actuation by a finger other than the thumb), repositioning of the control button 206 (e.g., for actuation by a finger other than the finger illustrated in FIGS. 3A-C), additional control buttons, and a variety of other features will fall within the scope of the present disclosure.

In an embodiment, the input from the user at block 402 of the method 400 may include one or more rotational inputs (i.e., a yaw input, a pitch input, and a roll input) and one or more translational inputs (i.e., movement along an x-axis, a y-axis, and/or a z-axis) that are provided by the user using, for example, the controllers. The user may reposition the first control member to provide rotational inputs and reposition the second control member to provide translational inputs. The controller is "unified" in that it is capable of being operated by a single hand of the user. In other words, the controller allows the user to simultaneously provide rotational and translational inputs with a single hand without cross-coupling inputs (i.e., the outputs from the hand controller are "pure").

As discussed above, the rotational and translational input may be detected using various devices such as photo detectors for detecting light beams, rotary and/or linear potentiometers, inductively coupled coils, physical actuators, gyroscopes, accelerometers, and a variety of other devices as may be known by one or more of ordinary skill in the art. A specific example of movements of the first control member and the second control member and their results on the control target 106 are discussed below, but as discussed above, any movements of the first control member and the second control member may be reprogrammed or repurposed to the desires of the user (including reprogramming reference frames by swapping the coordinate systems based on the desires of a user), and thus the discussion below is merely exemplary of one embodiment of the present disclosure.

Referring now primarily to FIGS. 3A-3C but with continued reference to the method 400 in FIG. 2 and the control system 100 in FIG. 1, the controller 200 is presented in more detail. In an embodiment, the controller 200 may be the controller 102 discussed above with reference to FIG. 1. The controller 200 includes a base 202 including a first control member mount 202a that extends from the base 202 and defines a first control member mount cavity 202b. The base 202 may be mounted to a support using, for example, apertures 202c that are located in a spaced apart orientation about the circumference of the base 202 and that may be configured to accept a fastening member such as a screw. Alternatively, a dovetail fitting with a guide-installation and release or other mechanical, magnetic, or other adhesive fixation mechanism known in the art may be utilized. A first control member 204, which may be the first control member 102a discussed above with reference to FIG. 1, is coupled to the base 200 through a base coupling member 204a that is positioned in the first control member mount cavity 202b, as illustrated in FIG. 3B. While in the illustrated embodiment, the coupling between the base coupling member 204a and first control member mount 202a is shown and described as a ball-joint coupling, one of ordinary skill in the art will recognize that a variety of other couplings between the base 202 and the first control member 204 will fall within the scope of the present disclosure. In an embodiment, a resilient member 205 such as, for example, a spring, may be positioned between the first control member 204 and the base 202 in the first control member mount cavity 202b in order to provide resilient movement up or down along the longitudinal axis of the first control member 204. Furthermore, a resilient member may be provided opposite the base coupling member 204a from the resilient member 205 in order to limit upward movement of the first control member 204. In some embodiments, the entrance to the first control member mount cavity 202b may be smaller than the base coupling member 204a such that the first control member 204 is secured to the base 202.

The first control member 204 includes an elongated first section 204b that extends from the base coupling member 204a. The first control member 204 also includes a grip portion 204c that is coupled to the first section 204b of the first control member 204 opposite the first section 204b from the base coupling member 204a. The grip portion 204c of the first control member 204 includes a top surface 204d that is located opposite the grip portion 204c from the first section of 204b of the first control member 204. In the illustrated embodiments, the top surface 204d of the grip portion 204c is also a top surface of the first control member 204. The grip portion 204c defines a second control member mount cavity 204e that extends into the grip portion 204c from the top surface 204d. A control button 206 is located on the first control member 204 at the junction of the first section 204b and the grip portion 204c. While a single control button 206 is illustrated, one of ordinary skill in the art will recognize that a plurality of control buttons may be provided at different locations on the first control member 204 without departing from the scope of the present disclosure.

A second control member 208, which may be the second control member 102b discussed above with reference to FIG. 1, is coupled to the first control member 204 through a first control member coupling member 208a that is positioned in the second control member mount cavity 204e, as illustrated in FIG. 3B. While in the illustrated embodiment, the coupling between the first control member coupling member 208a and first control member 204 is shown and described as a ball-joint coupling, one of ordinary skill in the art will recognize that a variety of other couplings between the first control member 204 and the second control member 208 will fall within the scope of the present disclosure. In an embodiment, a resilient member 209 such as, for example, a spring, may be positioned between the second control member 208 and the first control member 204 in the second control member mount cavity 204e in order to provide resilient movement up or down in a direction that is generally perpendicular to the top surface 204d of the grip portion 204c. In some embodiments, the entrance to the second control member mount cavity 204e may be smaller than the first control member coupling member 208a such that the second control member 208 is secured to and extends from the first control member 204.

The second control member 208 includes a support portion 208b that extends from the first control member coupling member 208a. The second control member 208 also includes an actuation portion 208c that is coupled to the support portion 208b of the first control member 204 opposite the support portion 208b the first control member coupling member 208a. In the illustrated embodiments, the actuation portion 208c of the second control member 208 defines a thumb channel that extends through the actuation portion 208c of the second control member 208. While a specific actuation portion 208c is illustrated, one of ordinary skill in the art will recognize that the actuation portion 208c may have a different structure and include a variety of other features while remaining within the scope of the present disclosure.

FIG. 3B illustrates cabling 210 that extends through the controller 200 from the second control member 208, through the first control member 204 (with a connection to the control button 206), and to the base 202. While not illustrated for clarity, one of ordinary skill in the art will recognize that some or all of the features of the controller 102, described above with reference to FIG. 1, may be included in the controller 200. For example, the features of the rotational module 102d and the translation module 102e such as the detectors, switches, accelerometers, and/or other components for detecting movement of the first control member 204 and the second control member 208 may be positioned adjacent the base coupling member 204a and the first control member coupling member 208a in order to detect and measure the movement of the first control member 204 and the second control member 208, as discussed above. Furthermore, the controller processor 102c and the transmitter 102f may be positioned, for example, in the base 202. In an embodiment, a cord including a connector may be coupled to the cabling 210 and operable to connect the controller 200 to a control system (e.g., the control system 100). In another embodiment, the transmitter 102f may allow wireless communication between the controller 200 and a control system, as discussed above.

As illustrated in FIGS. 3A-C, the user may use his/her hand 402a to move the first control member 204 back and forth along a line A (e.g., on its coupling to the base 202 for the controller 200, by tilting the grip portion 204c of the first control member 204 along the line A relative to the bottom portion of the first control member 204 for the controller 200), in order to provide pitch inputs to the controller 200. As illustrated in FIGS. 3A-C, the user may use his/her hand 402a to rotate the first control member 204 back and forth about its longitudinal axis on an arc B (e.g., on its coupling to the base 202 for the controller 200, by rotating the grip portion 204c of the first control member 204 in space for the controller 200), in order to provide yaw inputs to the controller 200. As illustrated in FIGS. 3A-C, the user may use their hand 402a to move the first control member 204 side to side along a line C (e.g., on its coupling to the base 202 for the controller 200, by tiling the grip portion 204c of the first control member 204 along the line B relative to the bottom portion of the first control member 204 for the controller 300), in order to provide roll inputs to the controller 200. Furthermore, additional inputs may be provided using other features of the controller 200. For example, a resilient member 205 may provide a neutral position of the first control member 204 such that compressing the resilient member 205 using the first control member 204 provides a first input and extending the resilient member 205 using the first control member 204 provides a second input.

As illustrated in FIGS. 3A-C, the user may use the thumb 402b to move the second control member 208 forwards and backwards along a line E (e.g., on its coupling to the first control member 204), in order to provide x-axis inputs to the controller 200. As illustrated in FIGS. 3A-C, the user may use the thumb 402b to move the second control member 208 back and forth along a line D (e.g., on its coupling to the first control member 204), in order to provide y-axis inputs to the controller 200. As illustrated in FIGS. 3A-C, the user may use the thumb 402b to move the second control member 208 up and down along a line F (e.g., on its coupling to the first control member 204 including, in some embodiments, with resistance from the resilient member 205), in order to provide z-axis inputs to the controller 200. In an embodiment, a resilient member 209 may provide a neutral position of the second control member 208 such that compressing the resilient member 209 using the second control member 208 provides a first z-axis input for z-axis movement of the control target 106 in a first direction, and extending the resilient member 209 using the second control member 208 provides a second z-axis input for z-axis movement of the control target 106 in a second direction that is opposite the first direction.

The method 400 then proceeds to block 404 where a control signal is generated based on the user input received in block 402 and then transmitted. As discussed above, the controller processor 102c and the rotational module 102d may generate rotational movement output signals in response to detecting and/or measuring the rotational inputs discussed above, and the control processor 102c and the translation module 102e may generate translational movement output signals in response to detecting and/or measuring the translation inputs discussed above. Furthermore, control signals may include indications of absolute deflection or displacement of the control members, rate of deflection or displacement of the control members, duration of deflection or displacement of the control members, variance of the control members from a central deadband, and/or a variety of other control signals known in the art.) For example, control signals may be generated based on the rotational and/or translational input or inputs according to the BLUETOOTH® protocol. Once generated, the control signals may be transmitted as an RF signal by an RF transmitter according to the BLUETOOTH® protocol. Those skilled in the art will appreciate that an RF signal may be generated and transmitted according to a variety of other RF protocols such as the ZIGBEE® protocol, the Wireless USB protocol, etc. In other examples, the control signal may be transmitted as an IR signal, a visible light signal, or as some other signal suitable for transmitting the control information. (ZIGBEE® is a registered trademark of the ZigBee Alliance, an association of companies headquartered in San Ramon, Calif., USA).

The method 400 then proceeds to block 406 where a transceiver receives a signal generated and transmitted by the controller. In an embodiment, the transceiver 102 of the signal conversion system 104 receives the control signal generated and transmitted by the controller 102, 200. In an embodiment in which the control signal is an RF signal, the transceiver 104a includes an RF sensor configured to receive a signal according to the appropriate protocol (e.g., BLU-ETOOTH®, ZIGBEE®, Wireless USB, etc.).

In other embodiments, the control signal may be transmitted over a wired connection. In this case, the transmitter 102f of the controller 102 and the transceiver 104a of the signal conversion system 104 may be physically connected by a cable such as a universal serial bus (USB) cable, serial cable, parallel cable, proprietary cable, etc.

The method 400 then proceeds to block 408 where control program provided by the conversion processor 104b of the signal conversion system 104 commands movement based on the control signals received in block 406. In an embodiment, the control program may convert the control signals to movement commands that may include rotational movement instructions and/or translational movement instructions based on the rotational movement output signals and/or translational movement output signals in the control signals. Other discrete features such as ON/OFF, camera zoom, share capture, and so on can also be relayed. For example, the movement commands may specify parameters for defining the movement of the control target 106 in one or more DoF. Using the example discussed above, if the user uses their hand 402a to move the first control member 204 back and forth along a line A (illustrated in FIGS. 3A-C), the resulting control signal may be used by the control program to generate a movement command including a pitch movement instruction for modifying a pitch of the control target 106. If the user uses their hand 402a to rotate the first control member 204 back and forth about its longitudinal axis about an arc B (illustrated in FIGS. 3A-C), the resulting control signal may be used by the control program to generate a movement command including a yaw movement instruction for modifying a yaw of the control target 106. If the user uses their hand 402a to move the first control member 204 side to side along a line C (illustrated in FIGS. 3A-C), the resulting control signal may be used by the control program to generate a movement command including a roll movement instruction for modifying a roll of the control target 106.

Furthermore, if the user uses their thumb 402b to move the second control member 208 forward and backwards along a line E (illustrated in FIGS. 3A-C), the resulting control signal may be used by the control program to generate a movement command including an x-axis movement instruction for modifying the position of the control target 106 along an x-axis. If the user uses their thumb 402b to move the second control member 208 back and forth along a line E (illustrated in FIGS. 3A-C), the resulting control signal may be used by the control program to generate a movement command including a y-axis movement instruction for modifying the position of the control target 106 along a y-axis. If the user uses their thumb 402b to move the second control member 208 side to side along a line D (illustrated in FIGS. 3A-C), the resulting control signal may be used by the control program to generate a movement command including a z-axis movement instruction for modifying the position of the control target 106 along a z-axis.

The method 400 then proceeds to block 410 where the movement of the control target 106 is performed based on the movement commands. In an embodiment, a point of view or a virtual representation of the user may be moved in a virtual environment based on the movement commands at block 410 of the method 400. In another embodiment, an end effector, a propulsion mechanism, and/or a steering mechanism of a vehicle may be actuated based on the movement commands at block 410 of the method 400.

Figure 4A:
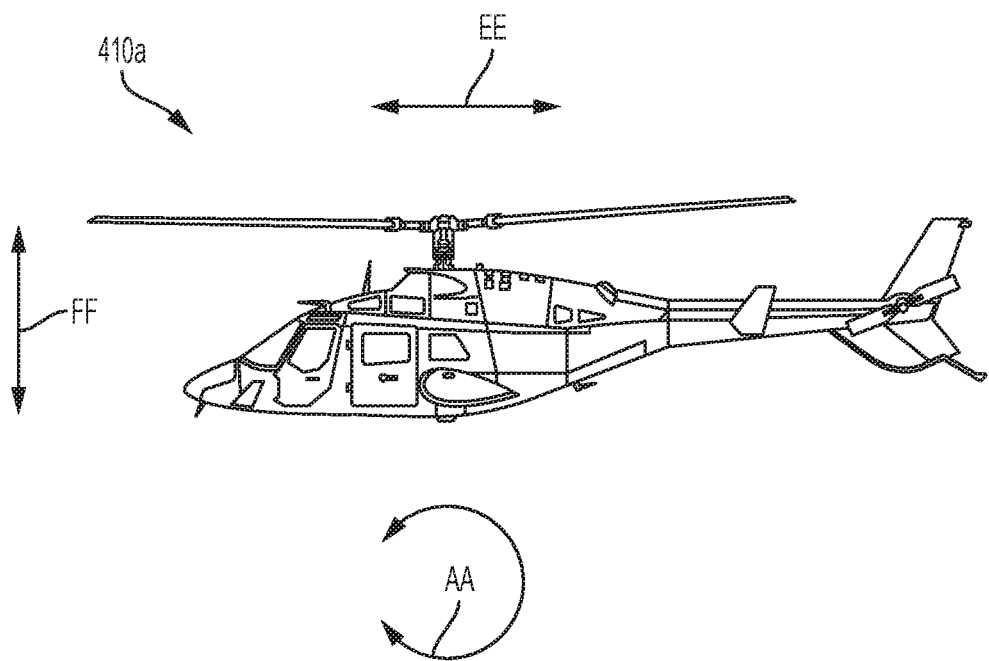
FIG. 4A is a side view illustrating an embodiment of a physical or virtual vehicle control target executing movements according to the method of FIG. 2.
Figure 4B:
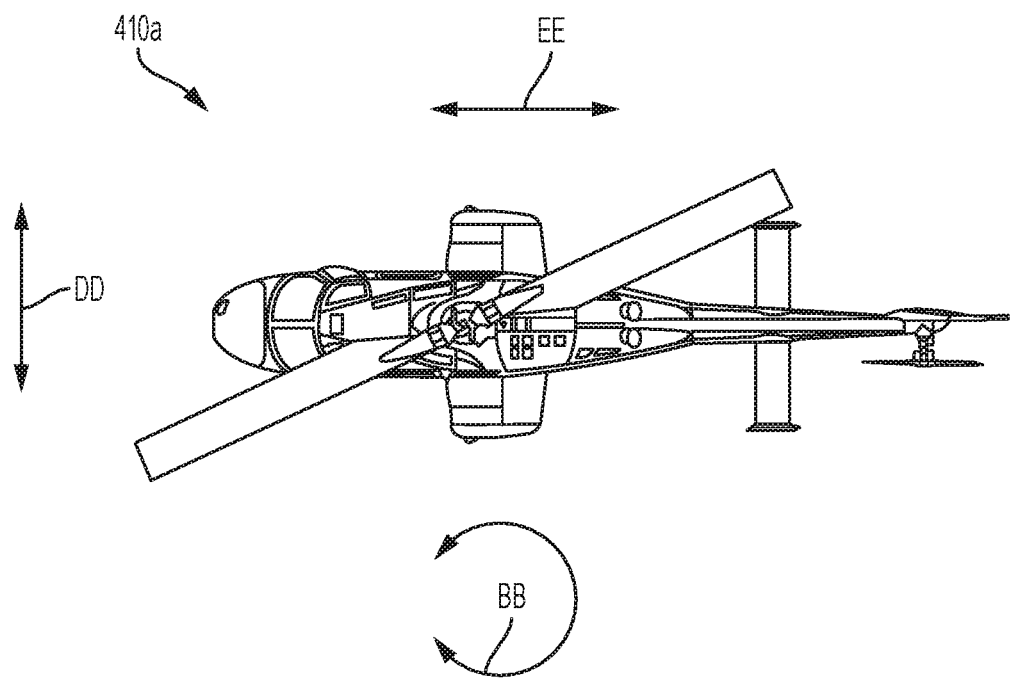
FIG. 4B is a top view illustrating an embodiment of the physical or virtual vehicle control target of FIG. 4A executing movements according to the method of FIG. 4A.
Figure 4C:
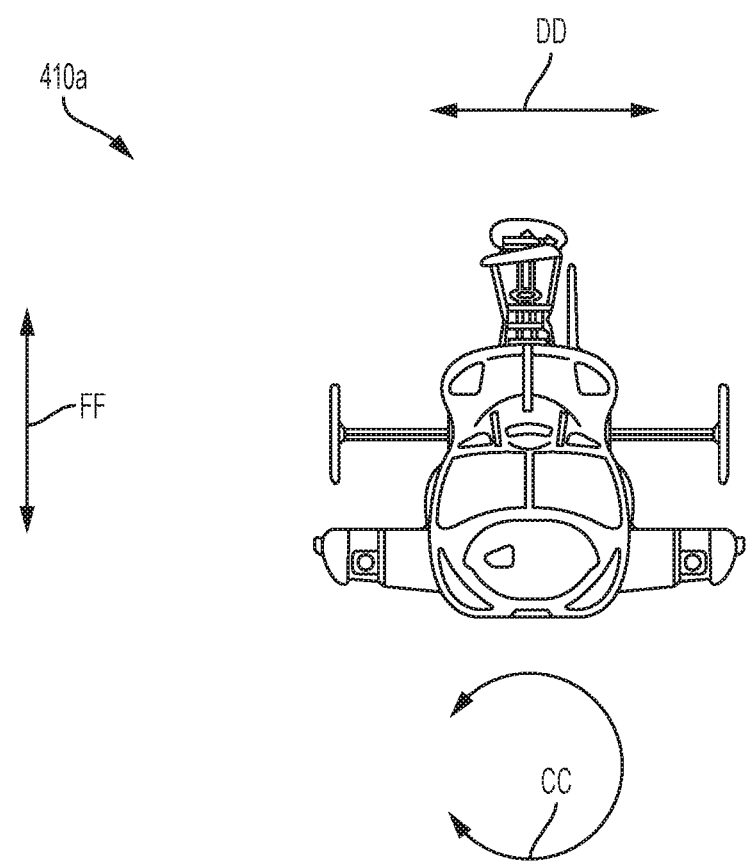
FIG. 4C is a front view illustrating an embodiment of the physical or virtual vehicle control target of FIG. 4A executing movements according to the method of FIG. 2.

FIG. 4A, FIG. 4B, and FIG. 4C illustrate a control target 410a that may be, for example, the control target 106 discussed above, with reference to FIG. 1. As discussed above, the control target 410a may include a physical vehicle in which the user is located, a remotely operated vehicle where the user operates the vehicle remotely from the vehicle, a virtual vehicle operated by the user through the provision of a point-of-view to the user from within the virtual vehicle, and/or a variety of other control targets as may be known by one or more of ordinary skill in the art. Using the example above (FIGS. 3A-C), if the user uses their hand 402a to move the first control member 204 back and forth along a line A (illustrated in FIGS. 3A-C), the movement command resulting from the control signal generated will cause the control target 410a to modify its pitch about an arc AA, illustrated in FIG. 4B. If the user uses their hand 402a to rotate the first control member 204 back and forth about its longitudinal axis about an arc B (illustrated in FIGS. 3A-C), the movement command resulting from the control signal generated will cause the control target 410a to modify its yaw about an arc BB, illustrated in FIG. 4B. If the user uses their hand 402a to move the first control member 204 side to side along a line C (illustrated in FIGS. 3A-C), the movement command resulting from the control signal generated will cause the control target 410a to modify its roll about an arc CC, illustrated in FIG. 4C.

Furthermore, if the user uses his/her thumb 402b to move the second control member 208 forward and backwards along a line E (illustrated in FIGS. 3A-C), the movement command resulting from the control signal generated will cause the control target 410a to move along a line EE (i.e., its x-axis), illustrated in FIG. 4B and FIG. 4C. If the user uses his/her thumb 402b to move the second control member 208 side to side along a line D (illustrated in FIGS. 3A-C), the movement command resulting from the control signal generated will cause the control target 410a to move along a line DD (i.e., its y-axis), illustrated in FIG. 4A and FIG. 4B. If the user uses his/her thumb 402b to move the second control member 208 back and forth along a line F (illustrated in FIGS. 3A-C), the movement command resulting from the control signal generated will cause the control target 410a to move along a line FF (i.e., its z-axis), illustrated in FIG. 4A and FIG. 4C. In some embodiments, the control button 206 and/or other control buttons on the controller 102 or 200 may be used to, for example, actuate other systems in the control target 410a (e.g., weapons systems.)

Figure 4D:
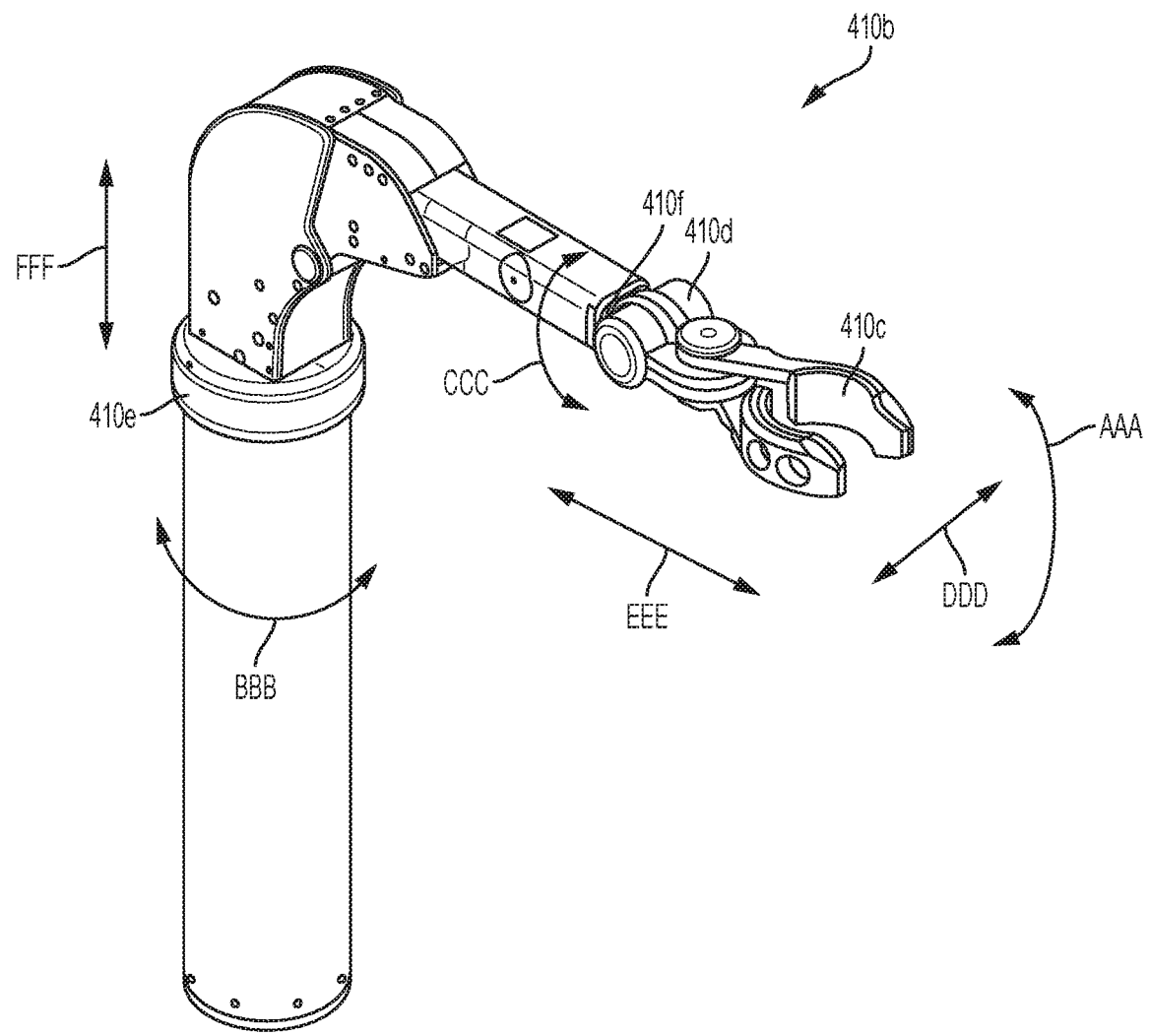
FIG. 4D is a perspective view illustrating an embodiment of a tool control target executing movements according to the method of FIG. 2.

FIG. 4D illustrates a control target 410b that may be, for example, the control target 106 discussed above, with reference to FIG. 1. As discussed above, the control target 410b may include a physical device or other tool that executed movements according to signals sent from the controller 102 or 200. Using the example above (FIGS. 3A-C), if the user uses their hand 402a to move the first control member 204 back and forth along a line A (illustrated in FIGS. 3A-C), the movement command resulting from the control signal generated will cause the control target 410*b* to rotate a tool member or end effector 410*c* about a joint 410*d* along an arc AAA, illustrated in FIG. 4D. If the user uses their hand 402*a* to rotate the first control member 204 back and forth about its longitudinal axis about an arc B (illustrated in FIGS. 3A-C), the movement command resulting from the control signal generated will cause the control target 410*b* to rotate the tool member or end effector 410*c* about a joint 410*e* along an arc BBB, illustrated in FIG. 4D. If the user uses his/her hand 402*a* to move the first control member 204 side to side along a line C (illustrated in FIGS. 3A-C), the movement command resulting from the control signal generated will cause the control target 410*b* to rotate the tool member or end effector 410*c* about a joint 410*f* along an arc CCC, illustrated in FIG. 4D.

Furthermore, if the user uses his/her thumb 402*b* to move the second control member 208 forwards and backwards along a line E (illustrated in FIGS. 3A-C), the movement command resulting from the control signal generated will cause the tool member or end effector 410*c* to move along a line EEE (i.e., its x-axis), illustrated in FIG. 4D. If the user uses his/her thumb 402*b* to move the second control member 208 back and forth along a line E (illustrated in FIGS. 3A-C), the movement command resulting from the control signal generated will cause the control target 410*b* to move along a line EEE (i.e., its y-axis through the joint 410*f*), illustrated in FIG. 4D. If the user uses his/her thumb 402*b* to move the second control member 208 side to side along a line D (illustrated in FIGS. 3A-C), the movement command resulting from the control signal generated will cause the tool member or end effector 410*c* to move along a line DDD (i.e., its z-axis), illustrated in FIG. 4D. In some embodiments, the control button 206 and/or other control buttons on the controller 102 or 200 may be used to, for example, perform actions using the tool member 210*c*. Furthermore, one of ordinary skill in the art will recognize that the tool member or end effector 410*c* illustrated in FIG. 4D may be replaced or supplemented with a variety of tool members (e.g., surgical instruments and the like) without departing from the scope of the present disclosure. As discussed above, the control target 410*a* may include a camera on or adjacent the tool member or end effector 410*c* to provide a field of view to allow navigation to a target.

Figure 5:
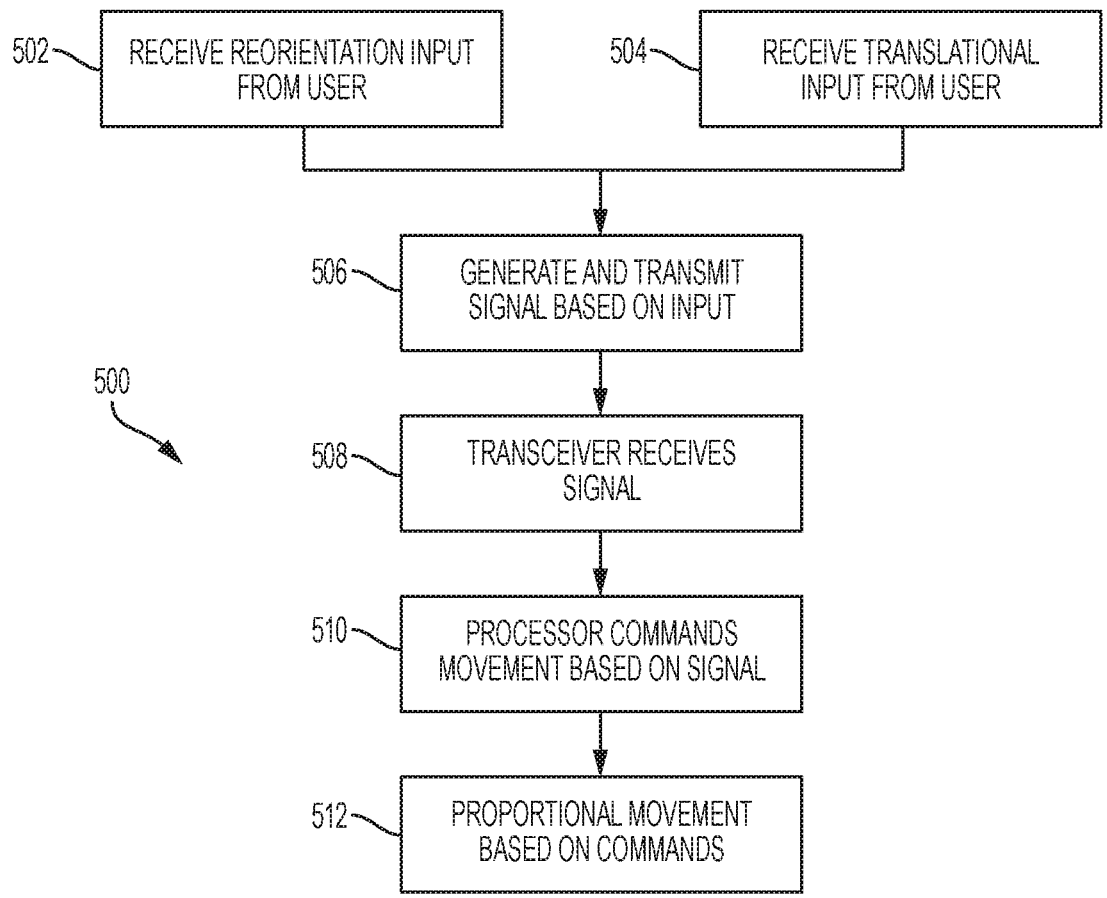
FIG. 5 is a flowchart illustrating an embodiment of a method for controlling a control target.

Referring now to FIG. 5, a method 500 for controlling a control target is illustrated. As is the case with the other methods described herein, various embodiments may not include all of the steps described below, may include additional steps, and may sequence the steps differently. Accordingly, the specific arrangement of steps shown in FIG. 5 should not be construed as limiting the scope of controlling the movement of a control target.

The method 500 may begin at block 502 where rotational input is received from a user. The user may provide rotational input by repositioning the first control member 204 of the controller 200 (FIGS. 3A-C) similarly as discussed above. In some embodiments, the rotational input may be manually detected by a physical device such as an actuator. In other embodiments, the rotational input may be electrically detected by a sensor such as an accelerometer.

The method 500 may proceed simultaneously with block 504 where translational input is received from the user. The user may provide translational input by repositioning the second control member 208 of the controller 200 similarly as discussed above. The rotational input and the translational input may be provided by the user simultaneously using a single hand of the user. In some embodiments, the translational input may be manually detected by a physical device such as an actuator.

In an embodiment, the rotational and translational input may be provided by a user viewing the current position of a control target 106 (FIG. 1) on a display screen. For example, the user may be viewing the current position of a surgical device presented within a virtual representation of a patient on a display screen. In this example, the rotational input and translational input may be provided using the current view on the display screen as a frame of reference.

The method 500 then proceeds to block 506 where a control signal is generated based on the rotational input and translational input and then transmitted. In the case of the rotational input being manually detected, the control signal may be generated based on the rotational input and translational input as detected by a number of actuators, which convert the mechanical force being asserted on the first control member 204 and the second control member 208 to an electrical signal to be interpreted as rotational input and translational input, respectively (FIGS. 3A-C). In the case of the rotational input being electronically detected, the control signal may be generated based on rotational input as detected by accelerometers and translational input as detected by actuators.

In an embodiment, a control signal may be generated based on the rotational input and translational input according to the BLUETOOTH® protocol. Once generated, the control signal may be transmitted as an RF signal by an RF transmitter according to the BLUETOOTH® protocol. One of ordinary skill in the art will appreciate that an RF signal may be generated and transmitted according to a variety of other RF protocols such as the ZIGBEE® protocol, the Wireless USB protocol, etc. In other examples, the control signal may be transmitted as an IR signal, visible light signal, or as some other signal suitable for transmitting the control information.

Referring still to FIG. 5 but with reference to FIG. 1, the method 500 then proceeds to block 508, the transceiver 104*a* of the signal conversion system 104 receives the control signal. In the case that the control signal is an RF signal, the transceiver 104*a* includes an RF sensor configured to receive a signal according to the appropriate protocol (e.g., BLUETOOTH®, ZIGBEE®, Wireless USB, etc.). In other embodiments, the control signal may be transmitted over a wired connection. In this case, the transmitter 102*f* and the transceiver 104*a* are physically connected by a cable such as a universal serial bus (USB) cable, serial cable, parallel cable, proprietary cable, etc.

The method 500 then proceeds to block 510 where the conversion processor 104*b* commands movement in 6 DoF based on the received control signal. Specifically, the control signal may be converted to movement commands based on the rotational and/or translational input in the control signal. The movement commands may specify parameters for defining the movement of a point of view or a virtual representation of the user in one or more DoF in a virtual 3D environment. For example, if the second control member is repositioned upward by the user, the resulting control signal may be used to generate a movement command for moving a point of view of a surgical device up along the z-axis within a 3D representation of a patient's body. In another example, if the first control member is tilted to the left and the second control member is repositioned downward, the resulting control signal may be used to generate movement commands for rolling a surgical device to the left while moving the surgical device down along a z-axis in the 3D representation of the patient's body. Any combination of rotational and translational input may be provided to generate movement commands with varying combinations of parameters in one or more DoF.

The method 500 then proceeds to block 512 where a proportional movement is performed in the virtual and/or real environment based on the movement commands. For example, a point of view of a surgical device in a virtual representation of a patient may be repositioned according to the movement commands, where the point of view corresponds to a camera or sensor affixed to a surgical device. In this example, the surgical device may also be repositioned in the patient's body according to the movement of the surgical device in the virtual representation of the patient's body. The unified controller allows the surgeon to navigate the surgical device in 6-DoF within the patient's body with a single hand.

Figure 6:
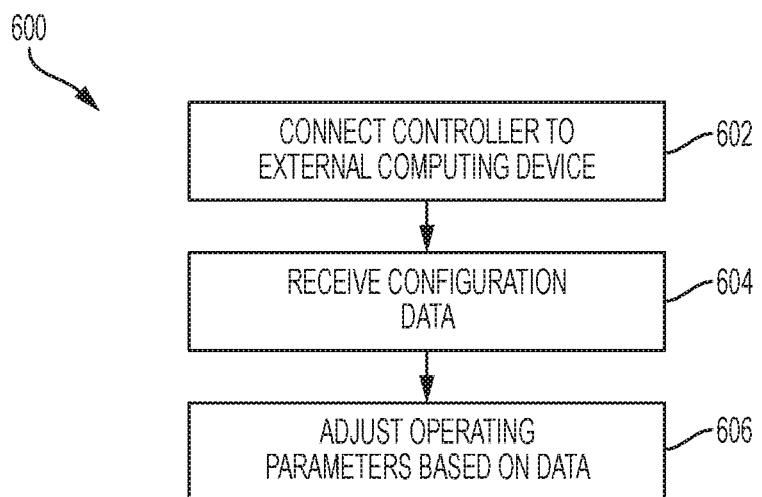
FIG. 6 is a flowchart illustrating an embodiment of a method for configuring a controller.
Figure 7:
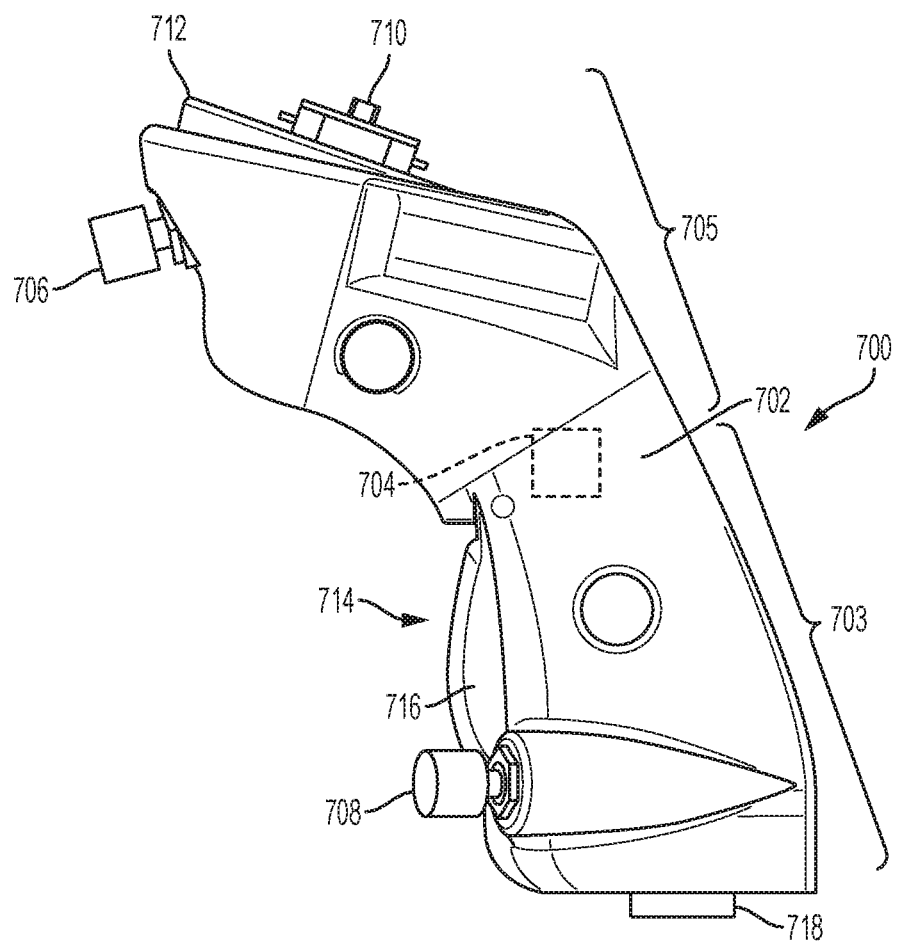
FIG. 7 is a side view of a first, representative embodiment of a single-hand controller.

Referring now to FIG. 6 with reference to FIG. 1, a method 600 for configuring a controller is illustrated. As is the case with the other methods described herein, various embodiments may not include all of the steps described below, may include additional steps, and may sequence the steps differently. Accordingly, the specific arrangement of steps shown in FIG. 6 should not be construed as limiting the scope of controlling the movement of a control target.

The method 600 begins at block 602 where the controller 102 is connected to an external computing device. The controller 102 may be connected via a physical connection (e.g., USB cable) or any number of wireless protocols (e.g., BLUETOOTH® protocol). The external computing device may be preconfigured with software for interfacing with the controller 102.

The method 600 then proceeds to block 604 where configuration data is received by the controller 102 from the external computing device. The configuration data may specify configuration parameters such as gains (i.e., sensitivity), rates of onset (i.e., lag), deadbands (i.e., neutral), and/or limits (i.e., maximum angular displacement). The configuration data may also assign movement commands for a control target to movements of the first control member and second control member. The configuration parameters may be specified by the user using the software configured to interface with the controller 102.

The method 600 then proceeds to block 606 where the operating parameters of the controller 102 are adjusted based on the configuration data. The operating parameters may be stored in memory and then used by the controller 102 to remotely control a control target as discussed above with respect to FIG. 2 and FIG. 5. In some embodiments, the method 600 may include the ability to set "trim", establish rates of translation (e.g., cm/sec) or reorientation (e.g., deg/sec), or initiate "auto-sequences" to auto-pilot movements (on a display or on the controller 102 itself.)

In other embodiments, the controller 102 may be equipped with an input device that allows the user to directly configure the operating parameters of the controller 102. For example, the controller 102 may include a display screen with configuration menus that are navigable using the first control member 204 and/or the second control member 208 (FIGS. 3A-C).

A computer readable program product stored on a tangible storage media may be used to facilitate any of the preceding embodiments such as, for example, the control program discussed above. For example, embodiments of the invention may be stored on a computer readable medium such as an optical disk e.g., compact disc (CD), digital versatile disc (DVD), etc., a diskette, a tape, a file, a flash memory card, or any other computer readable storage device. In this example, the execution of the computer readable program product may cause a processor to perform the methods discussed above with respect to FIG. 2, FIG. 5, and FIG. 6.

In the following examples of single hand controllers, various aspects allow the controller to separate individual translation from attitude adjustments in the control requirements of computer aided design, drone flight, various types of computer games, virtual and augmented reality and other virtual and physical tasks where precise movement through space is required, while simultaneously providing tactile feedback when away from the "null command" or zero input position.

For example, extended operation of a controller using the thumb for independent control inputs can lead to a "hitchhiker's thumb" fatigue issue. By adding a third control member, such as a linked paddle for the 3rd, 4th and 5th digits (or some sub-set of these) of the user's hand to squeeze or rotate while gripping the first control member, the second controller can be held up or pushed up (in +z direction), thus providing relief. Furthermore, the third control member and the second control member can be linked so that pushing down the second control member pushes out the paddle or third control member. As such, the thumb and accessory digits are in a dynamic balance, which can be quickly mastered. Alternatively, the index finger can be linked to provide counterbalance to the thumb. Users typically have finer motor control of their index finger, and therefore use of the index finger can provide the desired relief while also providing finer control over displacement along the Z-axis.

In other embodiments, the single hand controller can be used as part of a control system that has a wrist or forearm brace to serve as a reference for the rotational axes, particularly yaw that is difficult to measure with an inertial measurement unit (IMU). For example, although an IMU within the body of the first control member of the hand controller may work well for pitch and roll, but yaw can be noisy. Although this may be improved with software modifications, some exemplary embodiments described herein have a linkage to the wrist allows for potentiometers or optical encoders to measure all three rotational axes with precision. In some variants of a forearm brace implementation can use an index finger loop, used to open or close a grasp on an object in a virtual world.

The hand controller examples presented in connection with FIGS. 7-20B and their variations can be used in applications such as those presented above in the preceding section, such flight simulation, CAD, drone flight, and so on. Optional additional features, which may be used alone or, in several case, in combination with one or more of the other features, include: adjustable z spring forces and self-centering/zeroing capability; a relatively large x-y gantry on top of joystick for the second control member; a replaceable or resizable thumb loop for the second control member; forearm or wrist stabilization for ambulatory use (potentiometers, Hall effect sensors, or optical encoders for X/Y/Z translations, such as for use in drone applications and for integrating with virtual/augmented reality); and a mouse-based implementation for improved CAD object manipulation.

Referring now FIGS. 7 to 11, controllers 700, 900, 1000 and 1100 illustrate different, representative embodiments of a single-hand controller having three control members, one of which provides Z-axis secondary control.

The exemplary controllers 700, 900, 1000, 1000, as well as the controllers shown and described in FIGS. 12-20B, translational inputs for indicating movement along the X, Y and Z axes are preferably received from a user's thumb. The thumb is mapped to the brain in greatest detail relative to other parts of the hand. These controllers exploit its greater dexterity to provide input along the X, Y, and Z axes. As the thumb movements are relative to the first control member, which in these examples are in the form of a joy stick, translation can be decoupled from attitude control of the target control object. Squeezing a third control member located on the first control member allows any one or more of the second, third, fourth or fifth digits on a user's hand to support the user's thumb by applying an upward force or upward motion. The force and movement of the third control member is transmitted or applied to the second control member, and thus to the thumb, through an internal coupling.

These embodiments use an inertial measurement unit for measuring displacements of the first control member. However, as an alternative, these controllers can be adapted to use external sensors when the controller is mounted to pivot on a base, in which case sensors for sensing roll, pitch and yaw, could be located within the base, or when coupled with a user's wrist to provide a frame of reference, in which case one or more of the sensors for pitch, roll and yaw can be incorporated into the coupling. Examples of these arrangements are shown in later figures.

In the following description, the first control member may be generally referred to as a "joystick" or "control stick," as it resembles structurally a portion of previously known types of joysticks, at least where it is gripped, and functions, in some respects, as a might other types of joysticks because it is intended to be gripped by a person's hand and displaced (translated and/or rotated) or otherwise moved to indicate pitch, roll, and yaw, or motion. However, it should not imply any other structures that might be found in conventional joysticks and is intended only to signify an elongated structural element that can be gripped.

Referring now to the embodiment of FIGS. 7 and 8A, 8B, and 8C, controller 700 comprises a first control member, which may be referred to a joystick, having a pistol-grip-shaped body 702 formed by a grip portion 703, where it can be gripped at least two or more of the thumb and third, fourth and fifth fingers of a hand, and a top portion 705 located above where it is gripped. Within the first control member are one or more an integrated inertial measurement units (IMU) 704 (indicated only schematically with dashed lines because the internal structure with the body 702 is not visible in this view) to sense pitch, roll, and yaw control of the first control member. This embodiment includes an optional quick-connection 718 for connecting to a base or other structure. This particular embodiment also incorporates optional buttons, such as trigger 706 (positioned for operation by an index finger) and attitude hold button 708. That can be operated by digits on the hand holding the controller or by the user's other hand.

Mounted on top of the first control member, in a position that can be manipulated by a thumb of a person gripping the body 702 of the first control member, is mounted a second control member. The second control member comprises a gantry arrangement 710 for the user to displace fore and aft, and left to right, to generate an input to indicate movement along a y-axis and an x-axis, as well displace up or down to generate an input to indicate movement along a z-axis. In this particular example, the gantry arrangement 710 is mounted on a platform 712 that moves the gantry arrangement up and down. Although different ways of moving the platform (or the gantry 710), up and down can be employed, this particular example places the gantry 710 at one end of the hinged platform 712. This allows the gantry arrangement to move up and with respect to the first control member. Pushing down on the gantry displaces the platform 712 downwardly, thereby indicating an input for Z-axis control, while pulling up on the thumb loop (not shown) moves in the opposite direction along the Z-axis.

Part of the Z-axis input arrangement on this controller also includes in this example a third control member 714. In this example the third control member takes the form of a paddle 716 where the second, third, fourth and/or fifth finger on a user's hand is located when gripping the first control member around the body 702, so that the paddle 716 can be selectively squeezed by the user when gripping the controller. The paddle 716 and the platform 712 can be spring loaded so that they are in a zero position to allow for z-axis input to indicate motion in either direction from the zero position. The third control member acts as a secondary Z-axis control. The third control member is linked or coupled with the second control member. The inclusion of a third control member, such as the finger paddle 716, "balances" the second control member, helping to relieve hitch-hiker thumb fatigue in the user and gives finer motor control of user input along the Z-axis (up/down) while allowing also for simultaneous movement of the gantry along the X-axis and Y-axis.

Figure 8A:
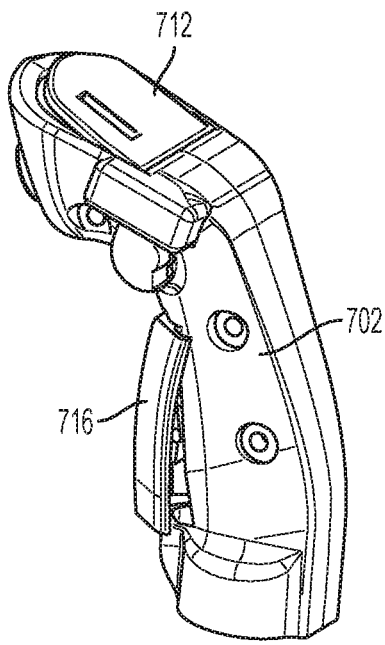
FIG. 8A is a perspective view of a second, representative embodiment of a single-hand controller that is partially assembled, with a pivoting platform for a second control member in a first position.
Figure 8B:
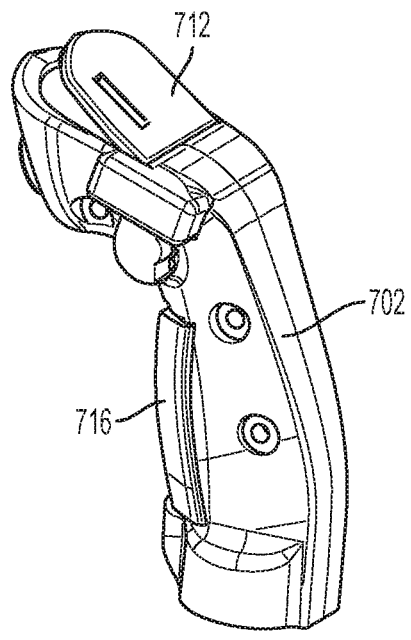
FIG. 8B is a perspective view of the second, representative embodiment of a single-hand controller that is partially assembled, with the pivoting platform for the second control member in a second position.

FIGS. 8A and 8B show controller 700 with a number of elements removed to more clearly show the cooperative movement of the paddle 716 and platform 712. In FIG. 8A, the platform is in a fully depressed position, and in FIG. 8B the platform 712 is in a fully extended position, the difference corresponding to the full travel of the second control member along a z-axis. In FIG. 8A the paddle 716 is in a fully extended position with respect to the body 702, and in FIG. 8B is fully depressed with respect to the body at 702.

Figure 8C:
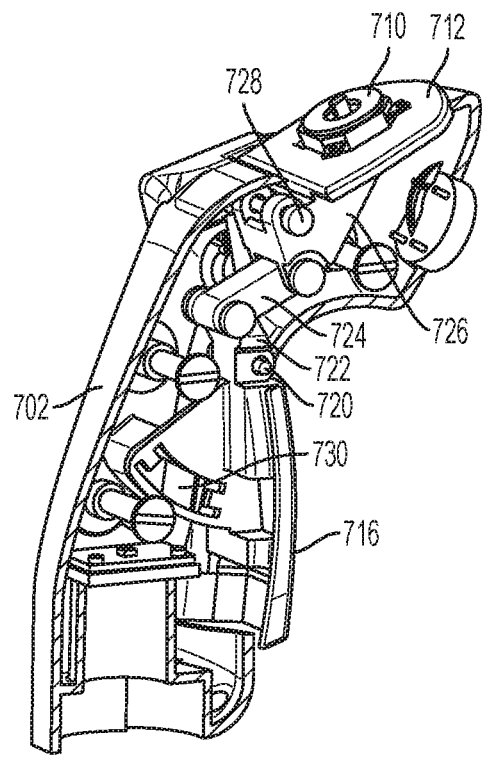
FIG. 8C is a perspective view of the second, representative is a perspective view of the second, representative embodiment of a single-hand controller in a different state of assembly than shown in FIGS. 8A and 8B, with one-half of a housing forming a first control member removed.

As shown in FIG. 8C, which is a perspective view of the controller 700 with one-half of the body removed along with most of its other internal components to reveal one example of a mechanical linkage. In this example, paddle 716 pivots about a pivot axis 720. A lever 722 connected with the paddle 716, but opposite of it with respect to the pivot axis 720, is pivotally connected to a linkage 724. The other end of linkage 724 is connected to a lever arm 726, to which platform 712 is connected. Platform 712 pivots about a pin forming an axis 728. Although not shown in the figure, a spring can be placed in an area indicated by reference number 730 to bias the paddle 716, and thus the entire linkage, toward a zero or neutral position. Additional springs can also be used to provide balance and to bias the linkage to place the paddle and gantry in the zero positions on the Z-axis.

Turning to FIGS. 9, 10 and 11, controllers 900, 1000, and 1100 share the same external components that make up the first and third control members. Each has body 902 that forms the first control member and has, generally speaking, a shape like a joystick or pistol-grip that is intended to be gripped and held in the hand of a user. Each incorporates, like controller 700, paddles 904 (which pivot from the top, for example) that can be operated by one or more of the fingers of the user that is gripping the first control member. Each also has a programmable button 905, for which a second finger loop can be substituted.

Similarly, each has a second control member on top of the body. Each second control member includes a platform 906 that moves up and down (by way of a hinge or other mechanism) to provide the Z-axis input. However, each differs in the nature of the second control member. Controller 900 uses a thumb loop 908 mounted to a gantry 906 that can be displaced fore-aft and left-right to provide x and y axis input, while also enabling displacement of the gantry in both directions along the z-axis by raising and lowering the thumb. This thumb loop can, preferably, be made in different sizes using an insert (not shown) that can accommodate different sizes. The thumb loops shown on any of the controllers in this disclosure can be made resizable using an insert or other adjustable mechanism, if desired. Controller 1000 of FIG. 10 uses a control member 1002 similar to the one shown on FIG. 7. And controller 1100 of FIG. 11 uses a trackball 1102 mounted on platform 906 for x and y axis input. Pushing down on the track ball is a z-axis input. The paddle 904 is used to provide input in the other direction along the z-axis.

In each of the controllers 900, 1000, 1100, as well as the hand controllers illustrated in the remaining figures, the second and third control members are coupled by a mechanical linkage disposed within the body of the first control member, like linkage shown in FIG. 8C. The linkage of FIG. 8C is, however, intended to be representative of such linkages in general, as different arrangements and numbers of links can be used depending on the particular geometries of the various parts and elements. Although other types of couplings or transmissions could be used to transmit displacement and force between the primary and secondary z-axis control elements in any of the controllers shown and described in FIGS. 7-20B. These could be other types of types of mechanical transmissions (for example cables), as well as electrical and magnetic transmissions that transmit position and, optionally, force, and combination any two or more of these types. A mechanical linkage, however, has an advantage since it is relatively simple and reliable for providing a direct coupling between the two control members, and since it immediately communicates force and position to provide a comfortable dynamic balance.

Furthermore, all of the controllers shown in FIGS. 7-11, as well as those shown in FIGS. 12-20B, preferably have re-centering mechanisms for each degree of freedom to give the user a sense of "zero" or null command. When a control member is displaced along one of the degrees of freedom, it preferably generates a tactile feedback, such as force, shake or other haptic signal, of the control members to return them to a position for zero input (the zero position). The mechanisms can consist of a spring that simply reacts with a spring force, or they can be active systems that sense displacement and/or force, and generate a reactive motion, force, other type of vibration haptic feedback, or combination of them.

Although not shown in FIGS. 7-11, each of the controllers 700, 900, 1000 and 1100, as well as the other controllers shown in the remaining figures, include at least the elements shown in FIG. 1. For example, it includes sensors (for example, inertial measurement units, potentiometers, optical encoders, or the like) for sensing displacement of the first, second and third control members; a processor for processing signals from the sensors; and a transmitter for transmitting the input signals from the controller, which can be radio frequency, optical or wired (electrical or optical). Such sensors can take the form of inertial measurement units, potentiometers, optical encoders and the like.

In any of the embodiments of controllers described in connection with FIGS. 1 to 20B, user feedback can be supplied from the controller by one or more of a number of mechanisms. For example, haptic vibration can provide a subtle vibration feedback. Force feedback can provide feedback in some or all degrees of freedom. Ambient heat and air can provide radiant heating and blowing air. Virtual reality multi-sensory integration can generate precise control within the virtual world. Integrated audio can provide sound feedback from a control target, such as a drone or other target device. The controller can also provide surface heat and cold to give feedback through a heat and cooling sensation. The user interface (UI/UX) may, optionally, include an integrated touchscreen and visual indicators such as light, flashing colors, and so on.

Figure 12:
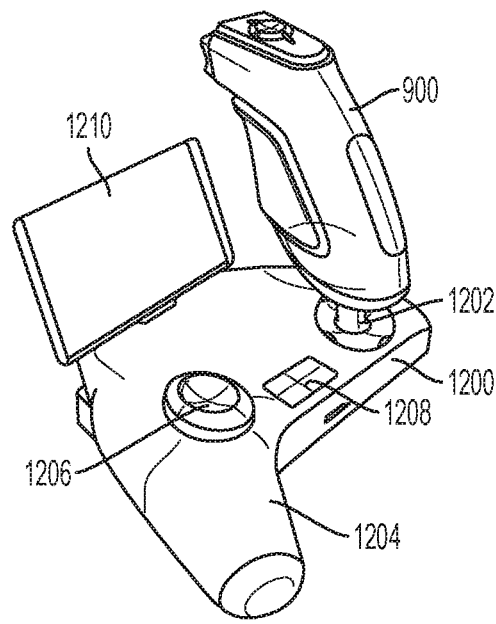
FIG. 12 is a perspective view of a mobile, two-handed control system having a controller mounted to a base.
Figure 13:
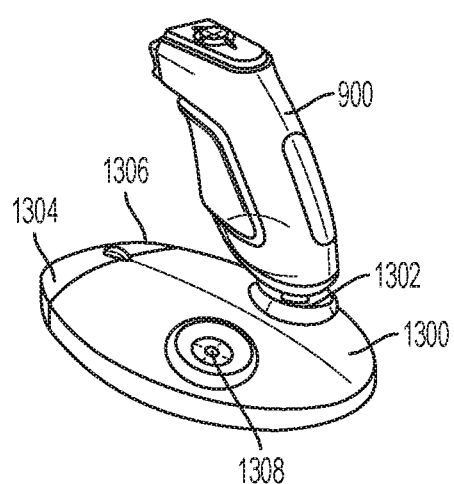
FIG. 13 is a perspective view of a controller mounted to a base having input buttons.
Figure 14:
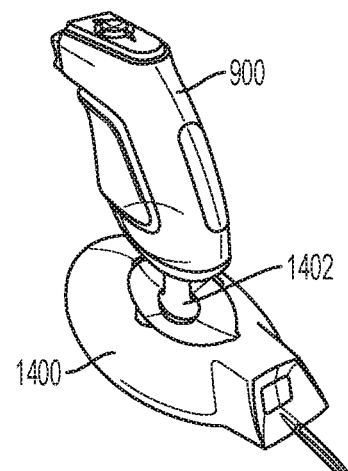
FIG. 14 is a perspective view of a single-handed controller mounted to a wired base.

Turning now to FIGS. 12, 13, and 14, shown are three variations of base structures 1200, 1300 and 1400 to which any one of controllers 700, 900, 1000, and 1100 can be connected. Those shown in any of the other figures, could be adapted as well. In the figures, controller 900 is used as an example, but the other controllers could be adapted for use with any of the bases. The bases may provide one or more of the following functions: as a frame of reference for measuring displacement of the first control member of the controller; for housing signal conditioning circuits for interfacing sensors for measuring displacement, a processor for running software programmed processes, such as those described above and elsewhere, a battery or other source for power, interfaces for other hardware, and transmitters and receivers for wireless communication.

FIG. 12 shows a mobile, two-handed controller system. A two-handed controller provides a consistent, known reference frame (stabilized by the non-dominant hand) even while moving, e.g., walking, skiing, running, driving. For certain types of applications, for example inspection, security and cinematographic drone missions, a hand controller may be mounted on a platform that can be held or otherwise stabilized by the user's other hand. The platform may include secondary controls and, if desired, a display unit. In one example, all 6-DoF inputs can be reacted through the platform. With such an arrangement, this example of a control system facilitates movement through the air like a fighter pilot with intuitive (non-deliberate cognitive) inputs.

A hand controller, such as hand controller 900, is plugged (or alternatively, permanently mounted), into the top surface of the base. A handle or grip 1204 in the shape of, for example, a pistol grip, is provided on the opposite side of the base for the user's other hand to grip while using the hand controller 900. (Other shapes and types of handles can also be envisioned by anyone skilled in the art.) This allows the user's other hand most likely the non-dominant hand, to hold or stabilize the base. The base may, optionally, incorporate additional user interface elements 1206 and 1208, such as keys, buttons, dials, touchpads, trackpads, trackballs balls, etc. Display 1210 is mounted on, or incorporated into, the base in a position where the user can view it. One or more videos or graphical images from the application being controlled can be displayed in real time on the display, such as live video from a drone, or a game. Alternatively, the base may include a mount on which a smartphone or similar device can be placed or mounted. Alternate or optional features include one or a combination of any two or more of the following features. The base can be reconfigurable for either hand with a quick disconnect for the joystick and two mounting points. It can be either asymmetric (as shown) or symmetric in shape, with ample room for secondary controls. It can include a smartphone attachment with tilt capability on its top surface. It may include secondary joystick to allow for pan and tilt control of the drone camera, and a capacitive or pressure deadman switch which may prevent or stop motion of the target when not engaged by a user gripping the joystick. It may also include large display mount and surface area for secondary controls. In an alternative embodiment a grip or handle can be located more midline to the controller, thus reducing some off-axis moments. In other embodiments, rather than holding the base it may be stabilized by mounting the base to the user's body. Example of mounting points for a base on a user's body include a chest mount, a belt, and an article of clothing.

FIG. 13 is an example of a base that can be moved to provide another input, in this case it is a mouse with additional input buttons 1304 and 1306. In this example, a secondary connection point 1308 for a hand controller is provided to accommodate both left and right-handed users. One example would be for navigation through 3-D images on a computer screen, where traditional mouse features would be used to move a cursor in the field of view, and to manipulate drop-down menus, while the controller 900 would be used to reorient and/or move the 3-D object in multiple degrees of freedom of motion.

FIG. 14 shows an example of a wired, fixed base, single handed controller 1400.

Although not required, each of the figures show an example embodiment in which the controller can be quickly connected at its bottom to the base. In each example of a base, the controller 900 is connected to a joystick-like, small lever (1202, 1302 and 1402). This lever could be used to provide pitch, roll and yaw input, with sensors located within the base, but it does not have to be. It can instead (or in addition) be used to center the first control member at a zero position and provide feedback to the user. An RF or wired connection between the controller and the base can be used to communicate signals from sensors within the controller.

Figure 15:
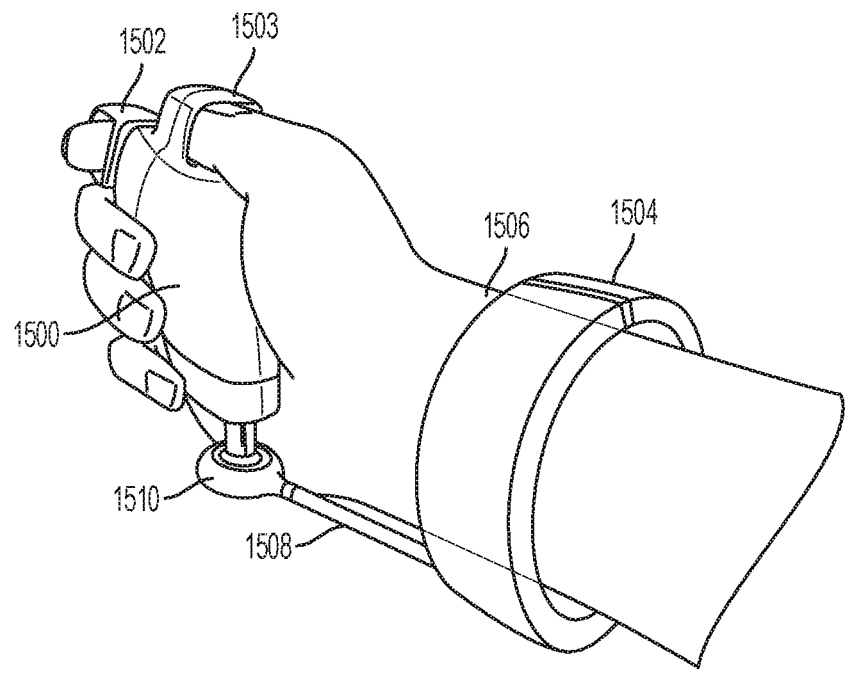
FIG. 15 is a perspective illustration of another, representative example and embodiment single-handed controller that is amounted to a bracket connected with a user's forearm.

FIG. 15 shows an example of an embodiment of a hand controller 1500, like controller 900, that includes an index finger loop 1502 in addition to a thumb loop 1503 that functions as a second control member. This index finger loop can be used to control opening and closing a physical or virtual end effector, say a hand grasp on an object in a virtual world. The design can ergonomically fit within the palm of the hand in very low profile and can be optimized for, virtual/augmented reality or drone flight. The addition of an index finger loop to open and close an end effector, for example, can benefit virtual/augmented reality applications.

Also, schematically shown in FIG. 15 is an attachment 1504 for placement on a forearm 1506 of a user. A coupling 1508 between the attachment 1504 and the hand controller 1500 supports the hand controller and allows for use of potentiometers or optical encoders to precisely measure angular displacement of pitch, roll, and yaw of controller 1500 when it is connected to a pivot point 1510 that is in a fixed relation to the forearm attachment 1504, even if removed from a base station. The indexing off of the wrist or forearm allows for this. In one embodiment, the hand controller does not use an IMU to sense one or more of the pitch, roll or raw, using instead the other types of sensors. Alternately the system can use two or more IMUs and software filtering of the data to measure relative displacement and to command flight control.

Moving any point of reference through physical or virtual space by way of a hand controller requires constant insight into displacement in every degree of freedom being controlled. Stated differently, it is important to know where "zero input" is at all times for movement along x, y, and z directions and yaw for a drone. Other flight regimes, such as virtual and augmented reality, computer gaming and surgical robotics may require as many as six independent degrees of freedom simultaneously (X, Y, Z, pitch, yaw, roll). Moreover, for drone flight and virtual reality and augmented reality in particular, the ability to be mobile while maintaining precise control of the point of reference (POR) is desirable.

In some embodiments, the index finger loop 1502 may be configured to constrain the index finger to prevent the index finger from moving. Constraining the index finger may provide stability and facilitate finer independent control of the thumb loop 1503 for the X, Y and Z translational movements.

FIGS. 15 to 20B illustrate several, representative embodiments of control systems having two parts: a hand-held controller and a forearm attachment in the form of a brace adapted or configured for mounting to a forearm or wrist of the user that provides a consistent, known reference frame (anchored to a user's wrist) even while the user or the user's arm is moving or accelerating, such as by walking, skiing, running, or driving.

In the examples shown in these figures, the forearm attachment might take any one of a number of forms. For example, it might comprise a brace, wrist wrap (which can be wrapped around a forearm or wrist and fastened using, for example, Velcro), slap-bracelet, or other items that conforms to at least a portion of the forearm. However, it may also comprise a relatively stiff support structure. The forearm attachment may be referred to as a brace, cuff or "gauntlet" because, structurally and/or functionally, it resembles these items in some respects.

However, use of these terms should not imply structures beyond what is shown or required for the statement function.

The hand controller and the forearm attachment are connected by a mechanical linkage, strut or support. In one embodiment, it is a passive linkage; in other embodiments it is not. One type of passive mechanical linkage used in the examples described below is a two-axis gimbal pivot with centering springs and potentiometers to measure displacement. Alternately, cables, double piston mechanisms (compression springs), pneumatic cylinders or passive stiffeners/battens, possibly built into a partial glove, could be used. In the examples, the linkage imparts a force to the user with which the user can sense zero input at least one, or at least two, or in all three axes of rotation on the joystick.

Small inertial measurement units (IMUs) may also be placed within the primary control member of a controller and forearm attachment, for example, allowing detection of pure differential (relative) motion between the forearm and the controller. Noisy signals could, for example, be managed by oversampling and subsequent decimation with digital adaptive filtering, thereby achieving measurement of relative motion of the hand versus the arm in mechanically noisy environments (while hiking, running or otherwise moving). However, in the embodiments described below that are able to measure one or more of pitch, roll or yaw with another mechanism, IMU's might only be needed one or two of the rotational displacements of the primary control member.

In an alternative embodiment, a passive or active mechanical feedback can be used to inform the user of displacement in a given axis of rotation might. The feedback may also include vibration haptics and force feedback.

For drone flight, one embodiment involves two gimbaled degrees of freedom at the wrist, and two at the thumb: wrist pitch (X or forwards/backwards) and wrist yaw (pivot left/right); thumb/Z paddle (translate up/down) and thumb Y (translate left/right).

Alternatively, displacement in roll of the forearm can be measured by physically sensing the movement of the radius bone over the ulna with a gauntlet that extends at least half way up the forearm. A full 6-degrees of freedom control, including measurement forearm roll, isn't necessary for drone flight, although it might be desirable for augmented reality applications. The yaw and Y translation inputs described above might be swapped, at user preference, based on flight testing and personal preference.

The thumb loop/"Z paddle" is preserved while using a "gantry" on top of the joystick to measure intended displacement laterally. Other methods of measuring forearm roll might include EMG detection of forearm muscle electrical potential, a conformal forearm wrap with pressure sensors that pick up differential contours of the forearm as a function of rotation, and differential IMUs or a combination of an IMU and a camera system (wrist vs elbow), showing rotation. The latter solutions would likely require vibration haptics or force feedback to inform the user of the zero position in roll.

One or more of the following features may be incorporated into any of the embodiments described herein: reconfigurable for either hand; symmetric shape with buttons available from either side; quick don and doff of wrist wrap or disconnect of joystick; smartphone attachment with tilt capability on wrist wrap; secondary joystick at the base of the joystick to allow for (pan)/tilt of the drone camera; a secondary joystick capable of retracting and extending from base of joystick like a ball point pen; capacitive or pressure activated dead man switch to make the controller fail-safe; a modular joystick that is able to be removed and placed on tabletop base, or operated standalone or on other types of function-specific bases, such as those described above.

Mechanisms that allow for pivoting of control members to indicate displacement in the various embodiments described herein, such as gimbals, may optionally include torsion springs for centering the control member and sensors, such as potentiometers and Hall effect sensors, for measuring angular displacement. Preferably, couplings or linkages that connect the joystick to a gimbal, for example, can be made adjustable or adaptable to accommodate joysticks of different sizes for different sized users.

A universal smart phone holder may also include a holder attached to a bracket mounted to the forearm attachment or brace.

The hand controllers in the following figures comprise six degrees-of-freedom single hand control device, with first control member in the form of joystick (or joystick like device), and second control member for the user's thumb (whether a loop, gantry, track ball, touch pad or other input device) has its Z-axis travel augmented by other third control member configured to be used by one or more fingers of the same hand and that move in conjunction with, and in opposition to, the second control member.

Further features useful in, for example, applications to drone flight or to virtual/augmented reality, can include a forearm brace to allow sensing of pitch, roll, and yaw using, for example, a mobile potentiometer, Hall effect, or optical encoder. Pan/tilt controls can also be integrated into the controller, as can a smart device (smartphone, tablet) holder. A base structure to which the hand controller is attached can also include a second handle for the user's other hand, or non-dominant hand, to allow for mobile potentiometer or optical encoder sensing.

Alternate solutions for yaw precision can include one or more of: induced magnetic field wrist bracelet, differential IMUs, software filtering of the IMU to reduce yaw related noise, reaction wheels (high precision gyro), and inertial (high precision yaw gyro) balanced yaw with potentiometers or optical encoders. Software filtering of IMU data can include dynamic re-zeroing.

The control signals from the controller can be further augmented by additional inputs. For example, a head or body mounted "connect sensor" can be used. This could use a grid-type infrared input or other optically based variations, such as RF directional or omnidirectional tracking. The connect sensors could be head mounted, such as for interactive virtual reality applications, or wrist mounted. "Dot" tracking can be used for more general body position inputs. The type of dot tracking can be, for example, magnetic or photogrammetric.

Figure 16:
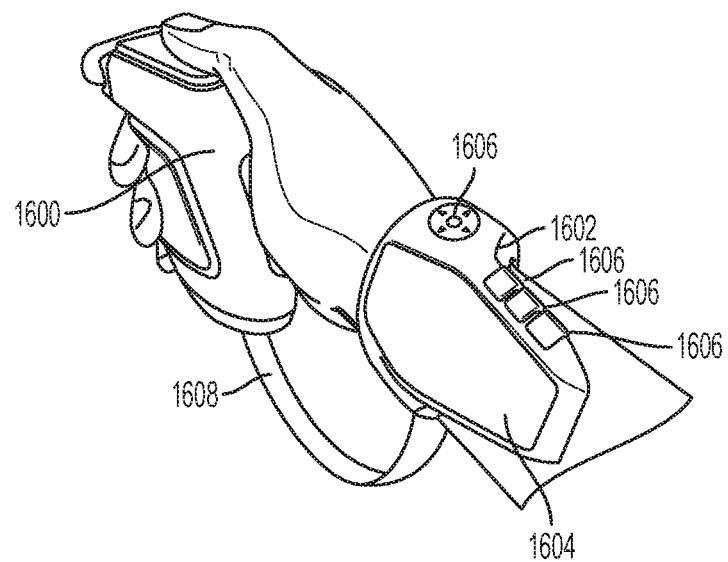
FIG. 16 is a perspective view of, yet another representative example and embodiment of a hand controller connected with to a forearm attachment worn by a user.

Referring now to FIG. 16, controller 1600 is substantially similar to other hand controllers described in the preceding paragraphs. In this example, it is connected to a forearm attachment 1602 that includes a video display 1604 and additional user inputs 1606 in the form of buttons and other types of user input. Connection 1608 between the and controller 1600 and the forearm attachment 1604 is a relatively stiff linkage that maintains the relative position of controller 1600 with the form attachment 1604, provide a pivot point around which pitch, yaw, and roll can be measured using either internal sensors or external sensors mounted at the end of connection 1608.

Figure 17:
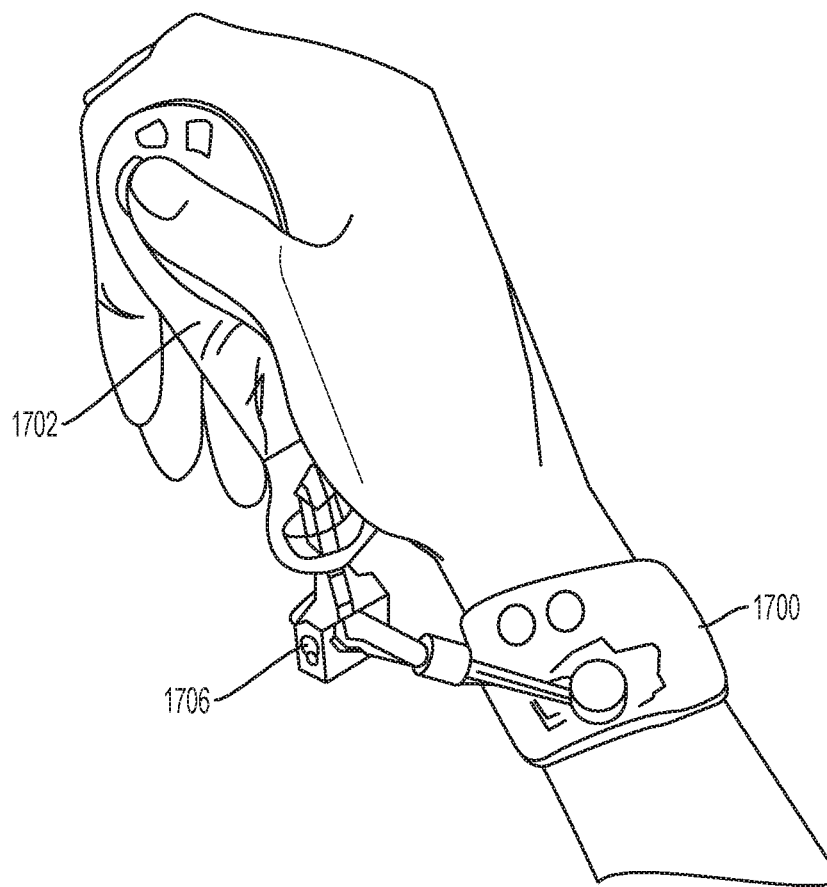
FIG. 17 is a perspective view of a representative example of a handle controller coupled with a cuff mounted on a user's forearm.
Figure 18:
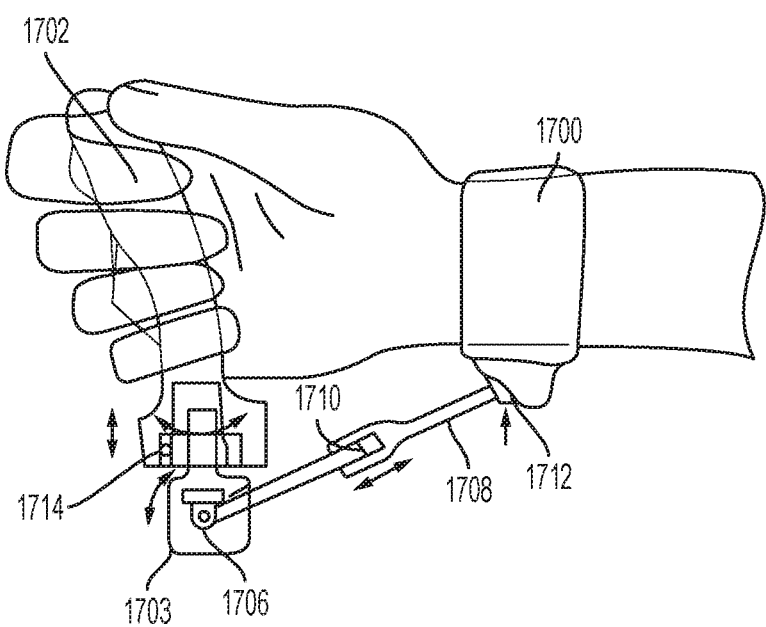
FIG. 18 is a side view of the representative example of a handle controller coupled with a cuff mounted on a user's forearm shown in FIG. 17.

Referring now to FIGS. 17 and 18, which illustrate an alternate embodiment of a cuff 1700 that acts as a forearm attachment. In this example, hand controller 1702 is schematically represented. It is representative of any of the hand controllers that have been described herein. Any of the hand controllers described herein can be adapted for use in this example. In this example, the controller is connected with a pitch sensor 1706 that is located below the controller and attached to the cuff 1700 with a mechanical link or strut 1708 that it is adjustable as indicated by length adjustment 1710. The end of the mechanical link 1708 is attached to the forearm attachment using a spherical bearing 1712 to allow for different angles. Like the length adjustment 1710, it will be tightened down once the user adjust the position of the controller to their satisfaction.

This example contemplates that an IMU is not be used in the controller, at least for pitch and yaw measurements. Rather, yaw, roll and pitch sensors are incorporated into the bottom of the hand controller 1702, or the base 1703 of a mechanical connection or support between the forearm attachment and the controller. Such sensors can take, in one example, the form of gimbal with one or more detectors, such as potentiometers or Hall effect sensors, and a spring (for example, a torsion spring) to provide feedback from zero position. In this example, a yaw sensor 1714 is incorporated into the bottom of the controller 1702, though it could also be incorporated into the base of the link or strut 1708 in which the pitch sensor 1706 is placed. A roll sensor, which is not visible, can be placed in either the base of the linkage 1708, in which the pitch sensor is placed, or in the bottom or base portion of the controller 1702.

Figure 19A:
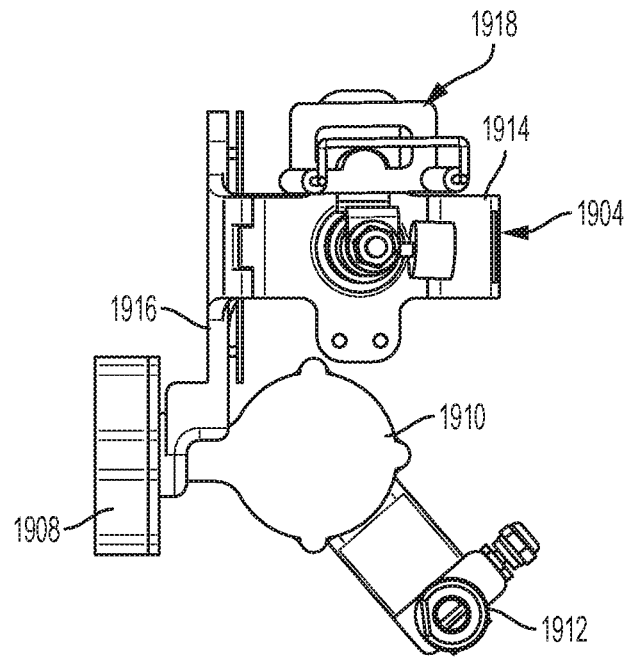
FIG. 19A is a top view of a representative example of a control system having a double-gimbal link between a forearm attachment and a hand controller.
Figure 19B:
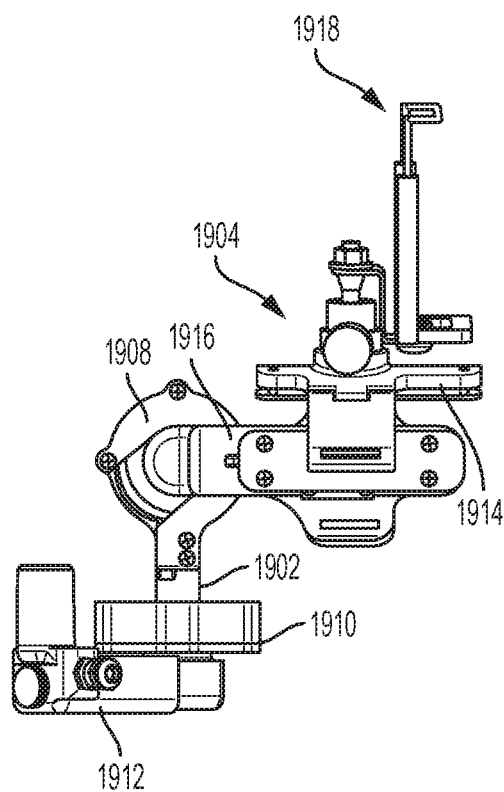
FIG. 19B is a side view of the control system of FIG. 19A.
Figure 19C:
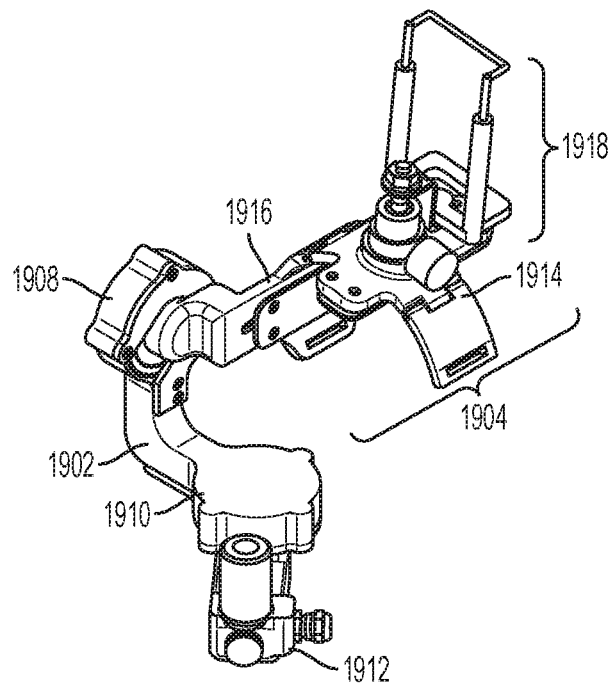
FIG. 19C is a perspective view of the control system of FIG. 19A.
Figure 19D:
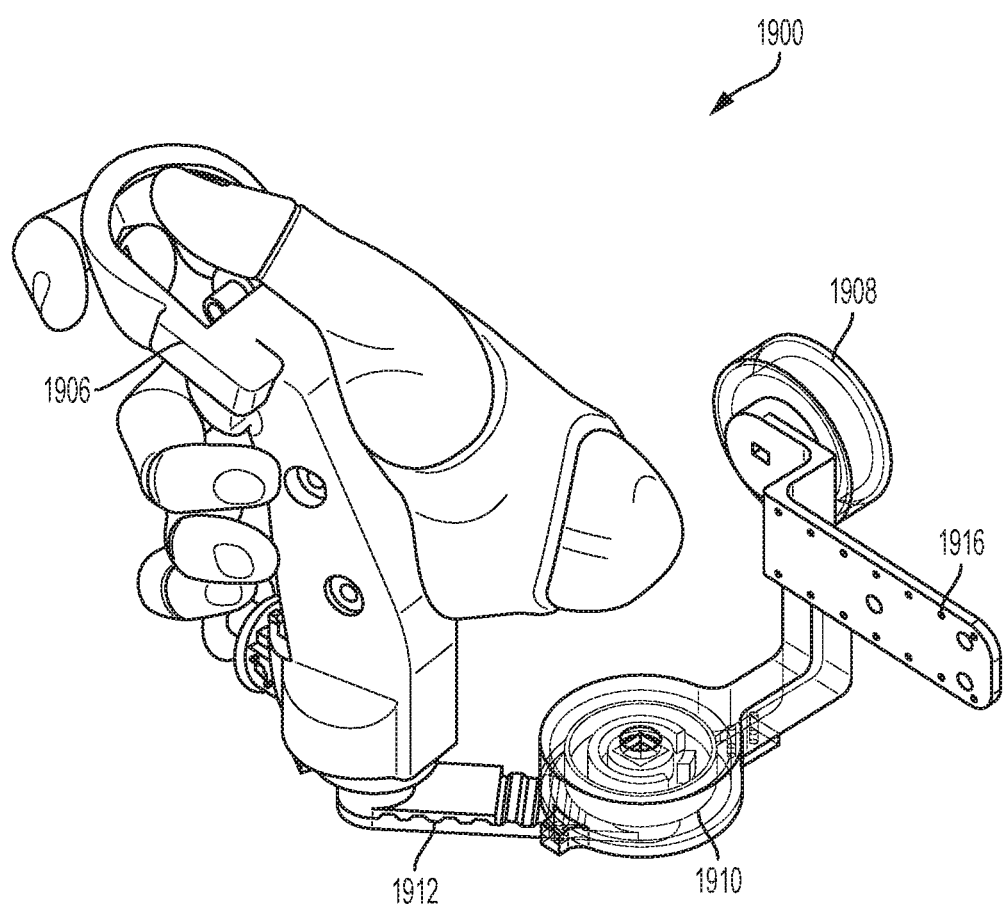
FIG. 19D is a perspective view of a second, representative example of a control system having a double-gimbal link between a forearm attachment and a hand controller.

Referring now to FIGS. 19A, 19B, 19C and 19D, illustrated is an embodiment of a control system 1900 with a specific example of a double gimbal link 1902 between a forearm attachment 1904 and a hand controller 1906 (FIG. 19D only). The double gimbal link 1902 attaches gimbals 1908 and 1910 placed at ninety degrees to each other to measure, respectively, pitch and yaw. The hand controller is connected to hand controller mount 1912 which acts as a lever arm and is connected to yaw gimbal 1910. The forearm attachment, which includes a sleeve or brace 1914, to which a strap may be connected to attach it to the arm, is supported on a lever arm 1916 that is connected to one side of the pitch gimbal 1908. Note that, in FIG. 19C. the hand controller mount 1912 that is shown is a variation of the one shown in FIGS. 19A and 19B, in that it is adjustable. A phone holder 1918 may be mounted or attached to the arm attachment 1904 so that it can be seen by the user. The phone holder is adjustable in this example so that it can hold different types and sizes of phones.

Figure 20A:
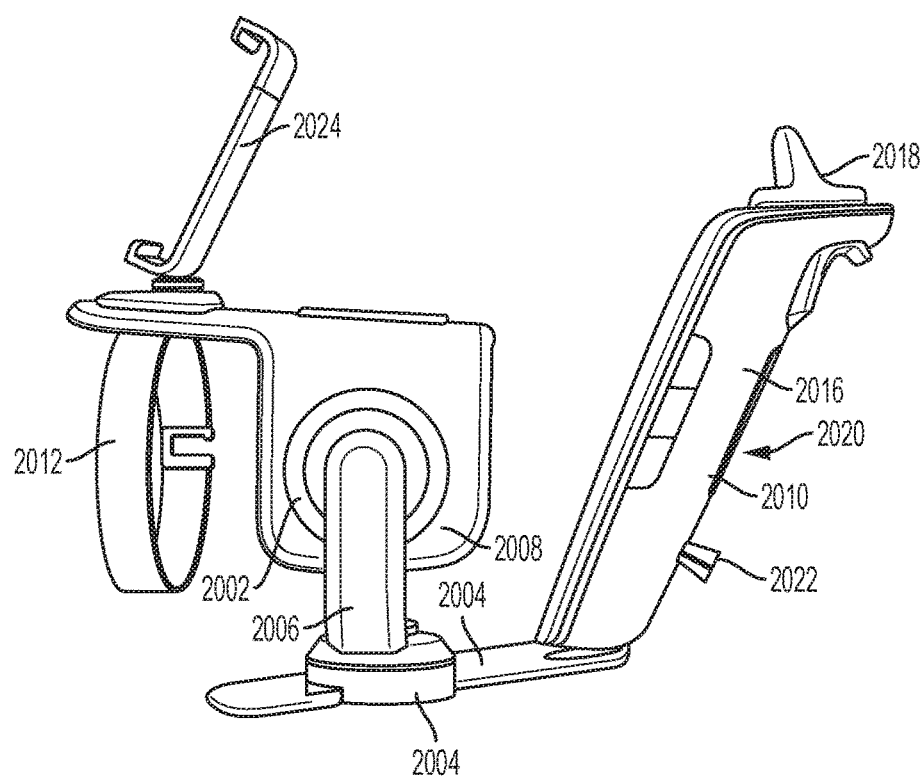
FIG. 20A is a side view of another, representative example of a control system of a control system having a double-gimbal link between a forearm attachment and a hand controller.
Figure 20B:
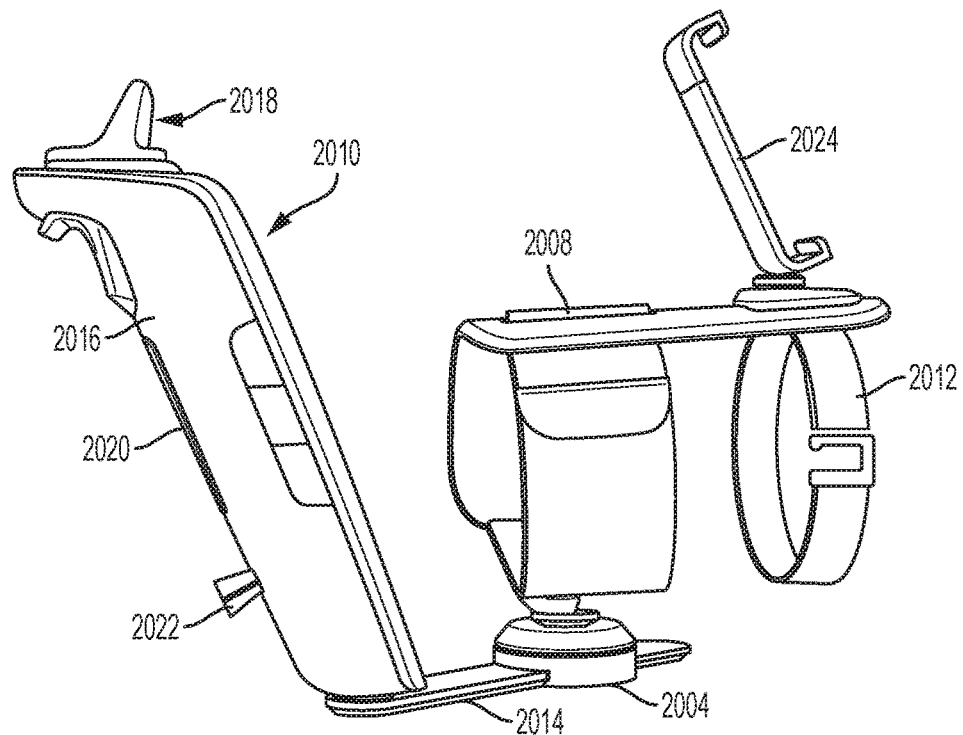
FIG. 20B is a different side view of the control system of FIG. 20A.
Figure 22A:
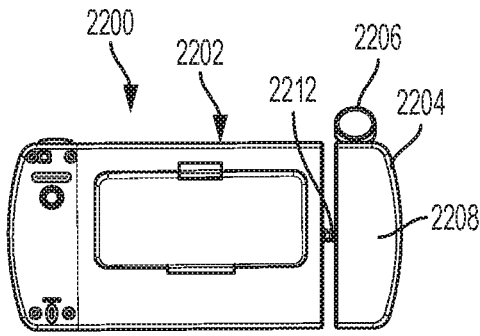
FIGS. 22A-22F illustrate a controller, according to an embodiment.
Figure 22B:
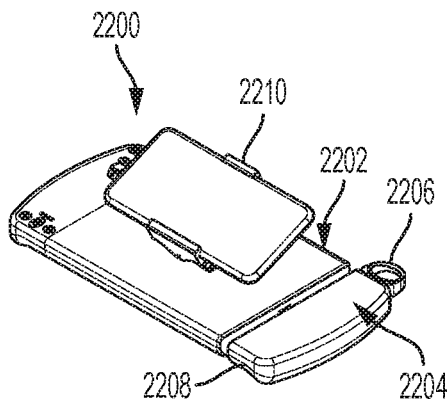
Figure 22C:
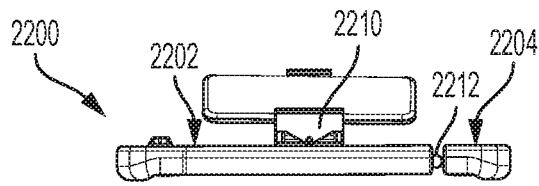
Figure 22D:
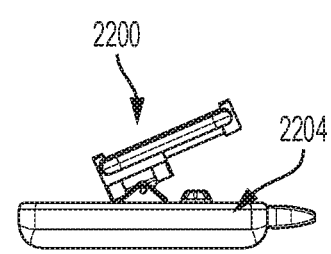
Figure 22E:
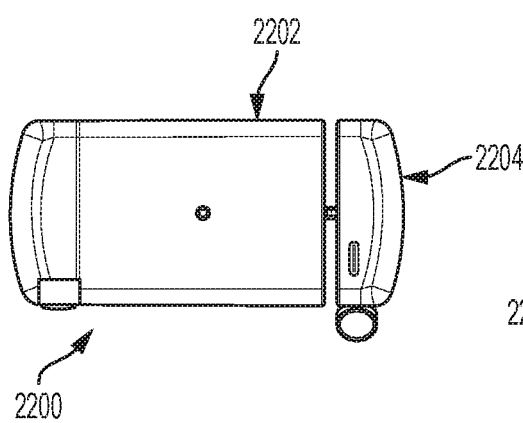
Figure 22F:
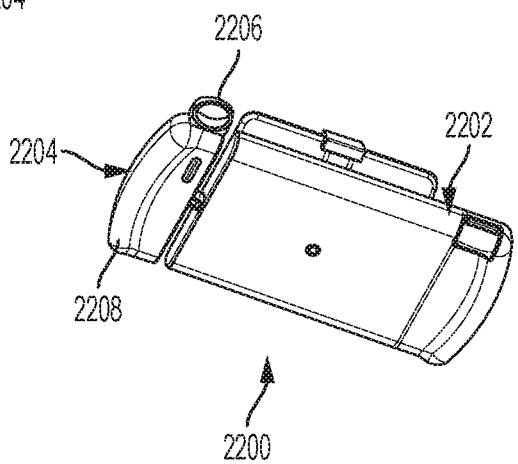

Turning now to FIGS. 20A and 20B, shown is another example of a control system similar to the one of FIGS. 19A-19D. In this example, the control system uses a pitch gimbal 2002 and a yaw gimbal 2004, which measure pitch and yaw, respectively, connected with a bracket 2006, in a manner similar to that shown in FIGS. 19A-19D. The pitch gimbal 2002 is mounted to a forearm attachment in the form of a brace 2008 placed near where the wrist joint pivots when gripping and rotating the controller 2010. The brace is held on by a strap 2012. The brace, as in the forgoing embodiments, acts as a stabilizer. The controller 2010 is mounted to an adjustable length lever arm 2014. In this example, controller 2010, like other hand controllers in the foregoing embodiments, has a body 2016 that forms a first control member that is graspable by the user that is used to input rotational displacements (two of which are measured by the gimbals), a second control member on top of the body 2016 in the form of a thumb loop 2018 for X, Y, Z input. On the front, near the bottom, of the body is a joy stick 2022, which can be used as input for camera pan and tilt, for example, or to manipulate tools.

Referring now to FIGS. 21A-21F, an illustrative embodiment of a two-handed controller system 2100 that is operable to be manipulated by a user's hand in up to 6 DoF is presented. The controller system 2100 is operable to be mobile and held by a hand of a user that is not gripping first control member 2106 e.g. the user's nondominant hand. However, the controller system 2100 may be positioned on the static surface or held against or mounted on a user's body by means of a harness, belt or other such method. The controller system 2100 includes a base structure 2102 and a single hand controller 2104. The controller system 2100 functions and operates in a manner like the controllers described above, such as at least the controllers 700, 900, 1000, 1100, and those described below. The controller 2104 includes, in addition to first control member 2106, a second control member 2108. The controller 2104 may further include a third control member (not shown) similar to other third control members described herein. The first control member 2106 is attached or coupled with the base to allow for rotationally displacement with respect to the base in up to three independent rotational degrees of freedom by a user gripping the first control member and pushing it. The second control member 2108 alone or in combination with the third control member, may be displaced along a Z axis.

The controller system 2100 further includes a mount 2110 on which a smart phone or similar device may be placed or mounted for communication with the target being controlled or to run an application for interacting with the controller system, such as to change parameters. The phone would, for example, communicate wirelessly with the base, although it could also be connected by wire to the base. The mount 2110 is comprised of a bracket having a first end connected to the base 2102 and a second end for mounting a smart phone. The mount 2110 may have an uppermost portion that extends above an uppermost portion of the hand controller 2104. The hand controller 2104 is angled towards the front of the base structure 2102 and the mount 2110 is angled towards the back of the base structure 2102. In other embodiments, the mount 2110 extends laterally past the back of the base structure 2102. The mount is, in one embodiment, adjustable to allow for positioning of the smartphone.

Referring now to FIGS. 22A-22F, an illustrative embodiment of a controller system 2200 that, like controller system 2100, with a single-handed controller that allows for input in 4 to 6 degrees of freedom while allowing the user's other hand to hold a base 2202. The controller system 2200 thus can be used in a mobile environment and held by a hand of a user other than the one gripping the first control member. The based 2202 of the controller system 2200 is shaped like a tablet. However, unlike the other control systems described herein, where one end of a hand controller is coupled at its lower one end for rotational displacement about a pivot point, the first control member in this embodiment is coupled to the base by a pivot 2202, such as a ball joint, gimbal or other device, near its mid-point to allow for rotational displacement in up to three degrees of freedom by pivoting or rotating it about up to three orthogonal axes extending through the pivot.

The controller 2200 functions similarly to previously disclosed controllers and others that are described herein. The controller 2204 includes a first control member 2206 that can be rotationally displaced in up to three degrees of freedom (or, in other embodiments, fewer than three degrees if desired) and a second control member 2208 that can be displaced in one to three degrees of freedom, depending on the embodiment. Although not shown, the controller 2204 may further include a third control member similar to other third control members described above and below. The controller system 2200 further includes a mount 2210 positioned on a top surface of the base structure 2202 for which a smart phone or similar device may be placed or mounted.

The hand controller 2204 is show in a stowed position with the hand controller 2204 oriented in a position parallel to the base structure 2202. For operation, the hand controller 2204 is rotated about a pivot 2212 into an operating position (not shown). The user may, in one embodiment, set a preferred null position once the rotated to the desired null operating position or that position could be set in advance and stored. Sensors for detecting rotational displacement of the first control can sense movement of the stowed position, though other sensors or switches can be used.

Figure 23:
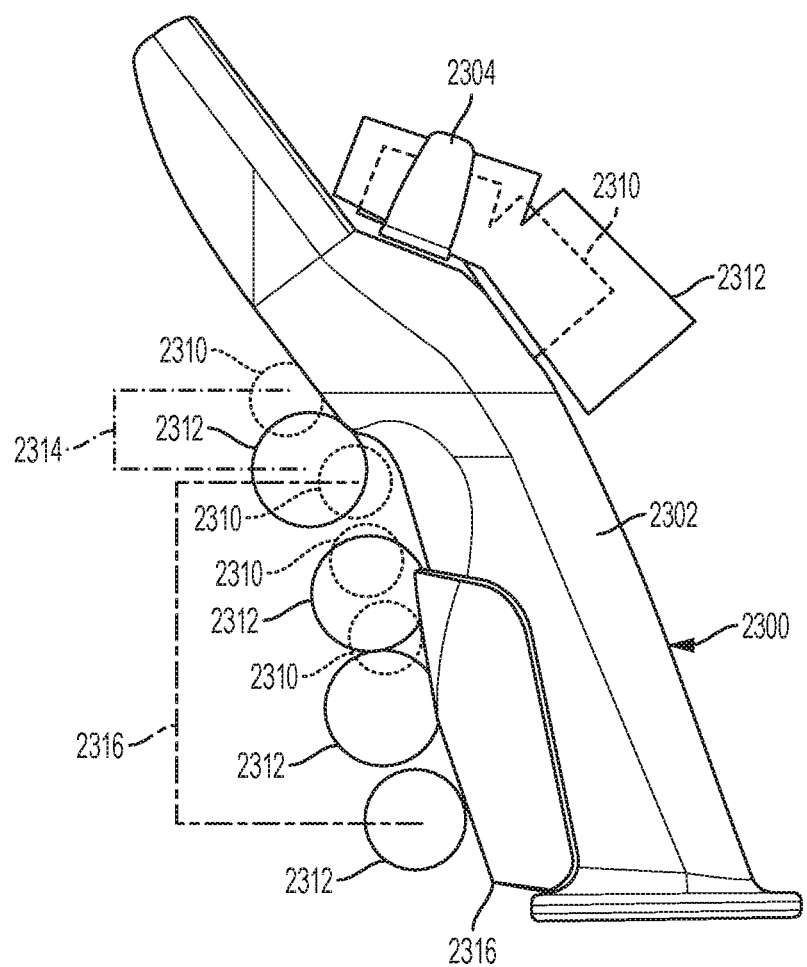
FIG. 23 is a side view of a hand controller.

Referring now to FIG. 23, a single hand controller like those described above and below can be designed with a third control member having a placement and size that can be controlled by hands of different sizes. Controller 2300 includes a first control member 2302, a second control member 2304, and a third control member 2306, each of which may operate or function like those of other controllers described above. A first hand 2310 is smaller than a second hand 2312. A first height 2314 represents a nonlimiting, approximate height range for index fingers of different sized hands. A second height 2316 represents nonlimiting, approximate height range for fingers 3, 4 and 5 of different sized hands. In an alternative embodiment, control number 2306 can be placed on a grip portion of the first controller at a higher location so that it can be depressed by an index finger of a user of different hand sizes.

Figure 24A:
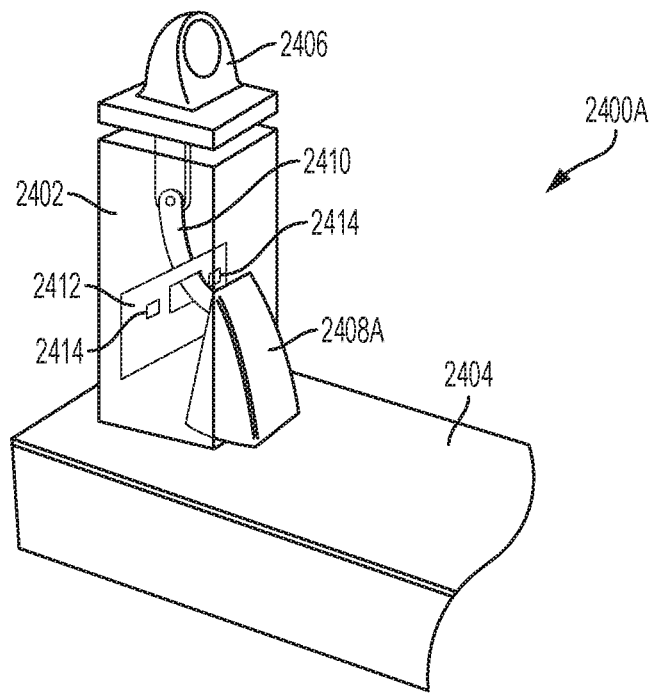
FIGS. 24A-24B schematically illustrate two versions of another embodiment of a hand controller.
Figure 24B:
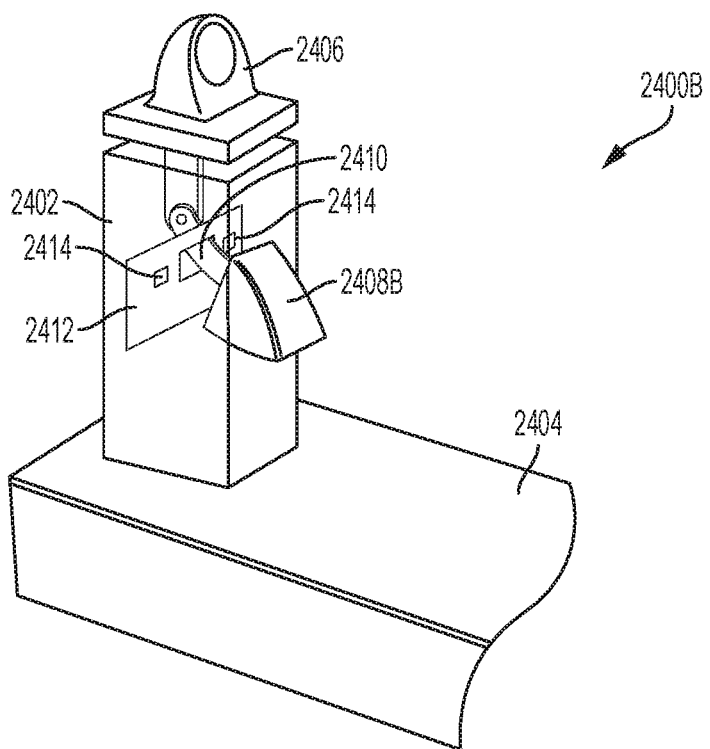

Referring now to FIGS. 24A-24B, shown are schematic illustrations for a 4 degree of freedom hand controller suitable for flying, for example, a drone aircraft. Two versions are shown, 2400A and 2400B. It is not shown connected to a base, but it would be connected with a base, or used with a forearm brace, as shown and described above. Each version is similar. Each has first control member 2402, which is intended to be gripped by the hand of a user, that is connected with a base 2404. Each has a second control member 2406 mounted on the first control member for displacement by a thumb or index finger of a user, though in the illustrations the second control member is in the form of a thumb loop. In other embodiments, the thumb loop can be replaced with another type of control member. The difference between them is the position on the first control member of a third control member, referenced as 2408A in FIG. 24A and 2408B in FIG. 24B. Third control member 2408A is positioned lower for operation by a user's third, fourth and/or fifth digits. Third control member 2408B is positioned higher, to be depressed or displaced by an index finger of a user gripping the first control member. Unlike other examples of hand controllers described herein, the second control member 2404 in each of the examples 2400A and 2400B moves in only one degree of freedom, along an axis that is generally oriented along the central axis of the first control member. The third control member 2406 is coupled to the second control member by linkage 2410 for enabling a user to dynamically balance the second and third control members. Applying force to on one of the control members applies a force to the other control member. A sensor is used to sense the direction of displacement of the second control member and the third control members. In this example, a circuit board 2412 within the first control member, on which is mounted one or more Hall effect sensors 2414 for sensing changes in a magnetic field generated by one or more magnets or other elements (not shown) on the linkage 2410 or one or the other (or both) of the second and third control members.

Figure 25A:
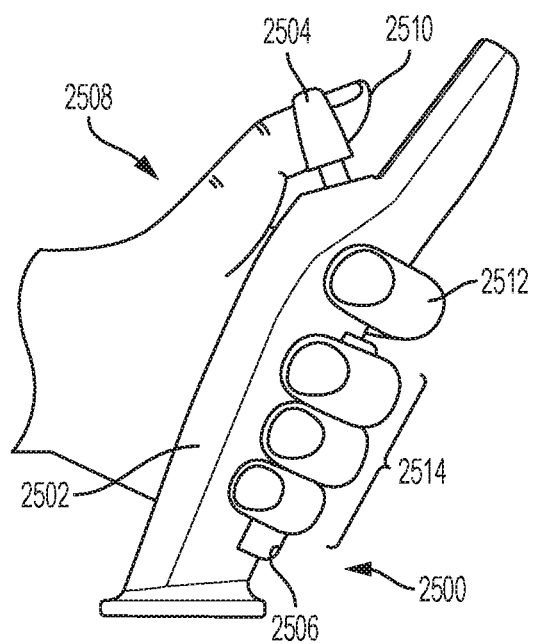
FIGS. 25A and 25B illustrated two positions of another embodiment of a hand controller.
Figure 25B:
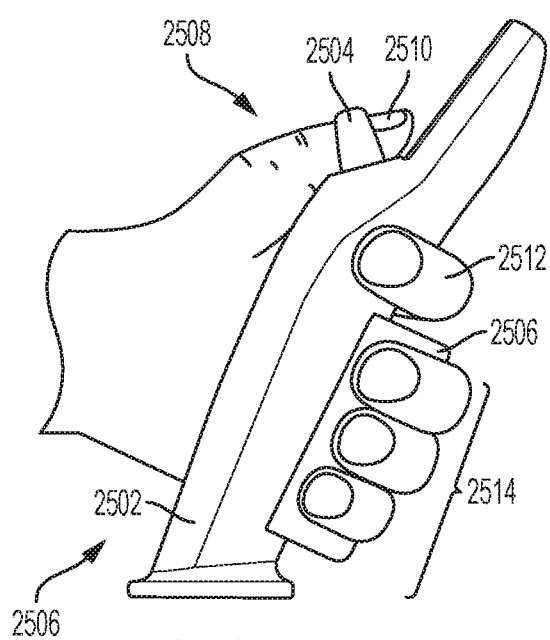

FIGS. 25A and 25B illustrate this dynamic balancing on hand controller 2500. A base is omitted, but it would be coupled with a base or forearm base like those described above, for sensor rotational displacement. Like those of FIGS. 24A and 24B, as well as several of the other hand controllers described above, the controller includes three control members: first control member 2502, second control member 2502, and a third control member 2506. A user's hand 2508 grips the first control member, in an area of the first member specially formed or adapted for gripping. The user's thumb 2510 is being used to displace the second control member 2504 along a Z axis. In this example, a thumb loop is used to allow the user's thumb to pull up on the second control member. However, the thumb loop does not have to be used. The third control member is mounted lower on the grip portion and large enough for any one or more of the users third, fourth or fifth digits 2514 to depress it inwardly, toward the first control member. Alternatively, it could have been mounted high enough to allow the user's index finger 2512 to depress it. In FIG. 25A, the second control member is extended upward, and the third control member is depressed. The user can cause this displacement by depressing the third control member, pulling up on the second control member, or a combination of both. In FIG. 25B, the second control member is pressed down, toward the first control member, causing the third control member to push outwardly from the from the first control member. The ability to push back on the third control member by squeezing with one or more fingers allows the displacement to be more easily controlled by the user than with the thumb alone.

In each of the controller systems 2100, 2200, and 2400, and hand controllers 2500 and 2600, as well as embodiments of several of the other controllers described herein, the hand controller's first control member can be rotationally displaced in up to three degrees of freedom (or, in other embodiments, fewer than three degrees if desired). Similarly, the hand controller's second control member may be adapted for displacement in one, two or up to three degrees of freedom, using a translational motion (such as up and down, along a Z axis, with respect to the first control member, as well as left and right, and fore and aft, along X and Y axes) and/or rotational motions about a pivot point for indicating displacement. Unless otherwise indicated, each control system could be adapted in alternative embodiments to allow for different degrees of freedom of displacement for each of its first and second control members. A third control member, if used, could, in one embodiment, be used to dynamically balance displacement of the second control member along the Z axis, which would be generally aligned with a central axis of the first control member. However, in alternate embodiments, displacement of the third control member could be used as another control input and not be linked to the second control member.

Figure 26:
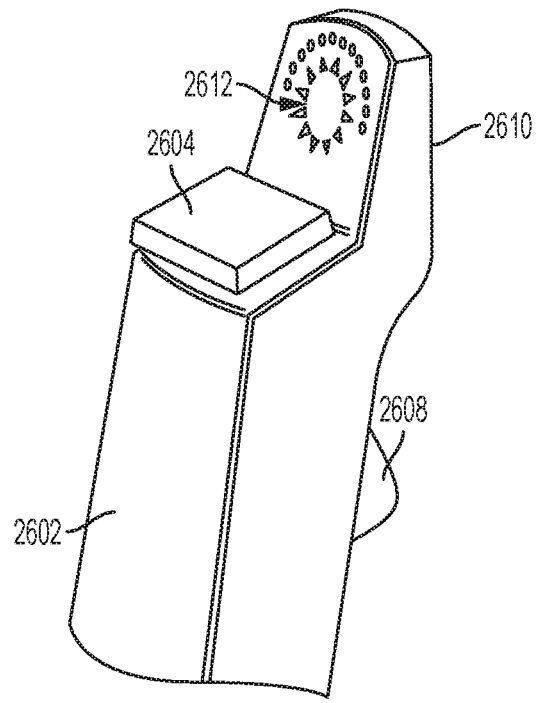
FIG. 26 is a schematic representation of another embodiment of a controller.

FIG. 26 is a schematic illustration of hand controller 2600 like controller 2500 shown in FIGS. 25A and 25B. It includes first, second and third control members 2602, 2604, and 2608, which operate like those described above in connection with other hand controllers. However, like controller 2500, the first control member includes an extension 2610 (integrally formed with it, in this example, though it could be a separate piece that is attached) on which there is a display that indicates information transmitted from a target, such as an aerial drone. Examples of information that it could display include direction of travel, altitude, and other positional or orientation information.

Figure 27:
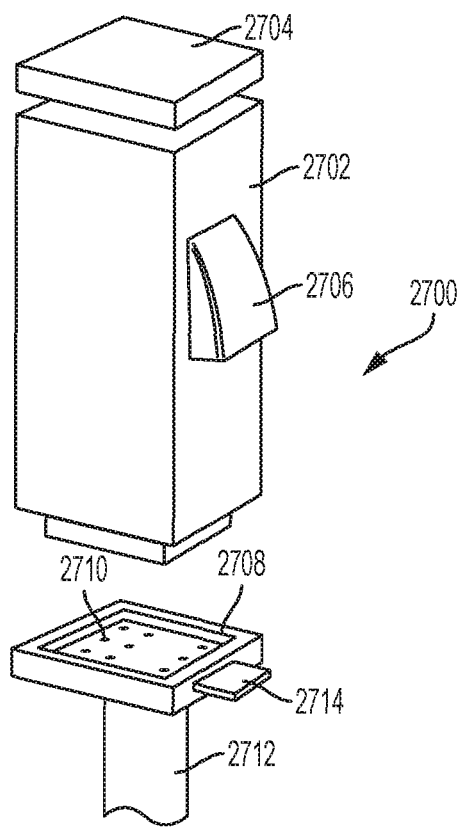
FIG. 27 is a schematic representation of a connector for releasable connecting a hand controller to base.

Referring now to FIG. 27, in the various examples of controller systems given above, each of the hand controllers is connected with a base, frame, brace or other element, against which the first control member is reacted to cause displacement around up to three axes of rotation and thus in up to three degrees of freedom, which also provides a frame of reference for measuring this displacement. In most of these exemplary embodiments, a handle controller, such as representative controller 2700, with a first control member 2702, a second control member 2704, and a third control member 2706, can, optionally, be configured or made to be removably attached to a base or other device using a connector. In this representative example, the bottom of the hand controller is plugged into a connector 2708. The connector may include contacts 2710 for making electrical connections to transmit signals and power to the hand controller. The connector is, in turn, connected with a post 2712 that is pivots using, for example, a rocker, ball, gimbal or other mechanism to sense rotational or angular displacement of the post in at least one degree of freedom, and up to three, mutually orthogonal axes with common origin at the pivot point. A button, detent or other retention mechanism, represented by button 2714 that operates a detent for engaging the base of the hand controller, can be used to hold and then release the hand controller from the connection. This particular example is intended to connect to a post of a ball joint or gimbal for allowing user displacement of the first control member.

Figure 28:
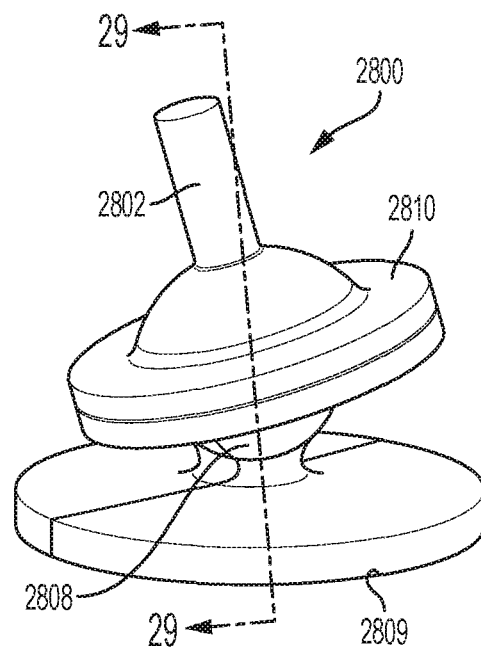
FIG. 28 illustrates schematically a gimbal.
Figure 29:
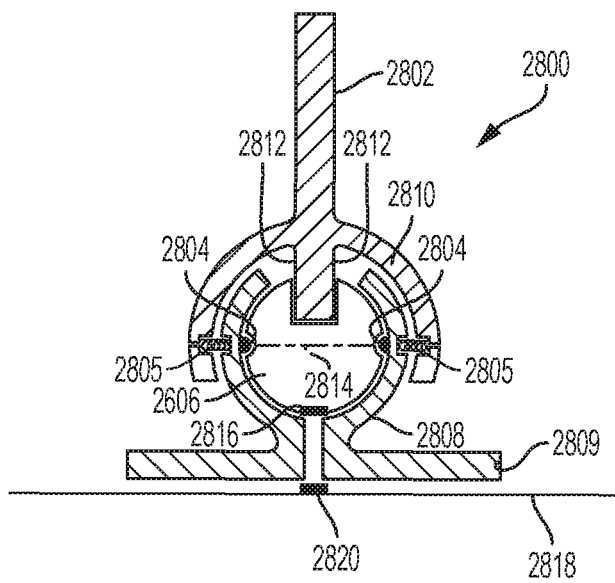
FIG. 29 is a cross-section of FIG. 28.

FIGS. 28 and 29 illustrated schematically an example of a gimbal 2800 that can be used with a sensor to allow for simultaneous displacement and measurement of displacement in two degrees of freedom of a control member, particularly a first control member. The gimbal can be mounted in a base, with a post 2802 for coupling it with a hand controller, or in the hand controller with the post connected to a base. The gimbal may also be adapted for use with a sensor for measuring displacement of the second control member.

In this particular example embodiment, the gimbal 2800 provides includes two detents 2804 in the form of balls that are biased inwardly against, for example by springs 2805, against ball 2806. Note that only one pair of detents are shown. The other pair would be oriented orthogonally to the pair that can be seen. Note that a single detent could be used for each direction of rotation, but a pair provides balance. Ball 2806 is mounted within a socket 2808 so that it can freely rotate within the socket in two degrees of freedom (though it can be used lock the ball to one degree of freedom of rotation). A base 2809 is representative of a structure for mounting the gimbal, against which the hand controller may react. A cap 2810 extends over the spherically-shaped outer surface of the socket so that it the post can pivot the cap. An extension or key 2812 fits within a complementary opening formed in the ball 2806 so that angular displacement of the post 2802 also rotates the ball. All detents engage the groove 2814 when the ball is rotated to the null position in both directions of rotation. The two pairs of detents engaging and disengaging provide tactile feedback to a user at null positions in two axes of rotation (pitch and roll, for example). To sensor rotation, one or more magnets 2816 are placed at the bottom ball 2806 (when in the null position.) This allows a PCB 2818 with at least one Hall effect sensor 2820 to be positioned closely to detect and measure angular displacement of the ball in the two rotational degrees of freedom and thereby generate a signal representative of the displacement. One advantage to this arrangement the springs and the joystick are higher up, keeping the bottom of the gimbal available for placement of a Hall effect sensor. Other types of sensors could be, in other embodiments, substituted for the Hall effect sensor and magnet. This gimbal mount could be used in other applications and not just the hand controllers described herein.

In the embodiments of a hand controller described above, when the hand controller is mounted to a base, the first control member is, for example, connected with a ball joint or gimbal for rotational displacement about up to three axes, and thus with up to three degrees of freedom. The base in the illustrated embodiments may also include the signal conditional circuits, processes, memory (for storing data and program instructions) and a source of power, as well as interfaces, wired and/or wireless, for communicating control signals generated by the controller system. FIG. 1 is a non-limiting example of such components.

Thus, systems and methods have been described that that include a controller that allows a user to provide rotational and translational commands in six independent degrees of freedom using a single hand. The system and method may be utilized in a wide variety of control scenarios. While a number of control scenarios are discussed below, those examples are not meant to be limiting, and one of ordinary skill in the art will recognize that many control scenarios may benefit from being able to provide rotational and translational movement using a single hand, even if fewer than all control outputs for all six degrees of freedom are required.

In an embodiment, the control systems and methods discussed above may be utilized in a wide variety of medical applications. While a number of medical applications are discussed below, those examples are not meant to be limiting, and one of ordinary skill in the art will recognize that many other medical applications may benefit from being able to provide rotational and translational movement using a single hand. Furthermore, in such embodiments, in addition to the rotational and translational movement provided using first and second control members discussed above, control buttons may be configured for tasks such as, for example, end-effector capture, biopsy, suturing, radiography, photography, and/or a variety of other medical tasks as may be known by one or more of ordinary skill in the art.

For example, the control systems and methods discussed above may provide a control system for performing laparoscopic surgery and/or a method for performing laparoscopic surgery. Conventional laparoscopic surgery is performed using control systems that require both hands of a surgeon to operate the control system. Using the control systems and/or the methods discussed above provide several benefits in performing laparoscopic surgery, including fine dexterous manipulation of one or more surgical instruments, potentially without a straight and rigid path to the end effector.

In another example, the control systems and methods discussed above may provide a control system for performing minimally invasive or natural orifice surgery and/or a method for performing minimally-invasive or natural-orifice surgery. Conventional minimally invasive or natural orifice surgery is performed using control systems that require both hands of a surgeon to operate the control system. Using the control systems and/or the methods discussed above provide several benefits in performing minimally invasive or natural orifice surgery, including fine dexterous manipulation of one or more surgical tools, potentially without a straight and rigid path to the end effector.

In another example, the control systems and methods discussed above may provide a control system for performing prenatal intrauterine surgery and/or a method for performing prenatal surgery. Conventional prenatal surgery is performed using control systems that require both hands of a surgeon to operate the control system in very tight confines. Using the control systems and/or the methods discussed above provide several benefits in performing prenatal surgery, including fine dexterous manipulation of one or more surgical tools, potentially without a straight and rigid path to the end effector.

For any of the above surgical examples, the control systems and methods discussed above may provide a very stable control system for performing microscopic surgery and/or a method for performing microscopic surgery. Using the control systems and/or the methods discussed above provide several benefits in performing microscopic surgery, including highly accurate camera and end effector pointing.

In another example, the control systems and methods discussed above may provide a control system for performing interventional radiology and/or a method for performing interventional radiology. Conventional interventional radiology is performed using control systems that require both hands of a surgeon to operate the control system. Using the control systems and/or the methods discussed above provide several benefits in performing interventional radiology, including highly accurate navigation through for interventional radiology. In another example, the control systems and methods discussed above may provide a control system for performing interventional cardiology and/or a method for performing interventional cardiology. Conventional interventional cardiology is performed using control systems that require both hands of an interventionist to operate the control system. Using the control systems and/or the methods discussed above provide several benefits in performing interventional cardiology, including highly accurate navigation through the vascular tree using one hand.

In another example, the control systems and methods discussed above may provide a control system including Hansen/Da Vinci robotic control and/or a method for performing Hansen/Da Vinci robotic control. Conventional Hansen/Da Vinci robotic control is performed using control systems that require both hands of a surgeon to operate the control system. Using the control systems and/or the methods discussed above provide several benefits in performing Hansen/Da Vinci robotic control, including fluid, continuous translation and reorientation without shuffling the end effector for longer motions.

In another example, the control systems and methods discussed above may provide a control system for performing 3D- or 4D-image guidance and/or a method for performing 3D- or 4D-image guidance. Conventional 3D- or 4D-image guidance is performed using control systems that require both hands of a surgeon to operate the control system. Using the control systems and/or the methods discussed above provide several benefits in performing 3D- or 4D-image guidance, including fluid, continuous translation and reorientation without shuffling the end effector for longer motions.

In another example, the control systems and methods discussed above may provide a control system for performing endoscopy and/or a method for performing endoscopy. Conventional endoscopy is performed using control systems that require both hands to operate the control system. Using the control systems and/or the methods discussed above provide several benefits in performing endoscopy, including fluid, continuous translation and reorientation without shuffling the end effector for longer motions. This also applies to colonoscopy, cystoscopy, bronchoscopy, and other flexible inspection scopes.

In an embodiment, the control systems and methods discussed above may be utilized in a wide variety of defense or military applications. While a number of defense or military applications are discussed below, those examples are not meant to be limiting, and one of ordinary skill in the art will recognize that many other defense or military applications may benefit from being able to provide rotational and translational movement using a single hand.

For example, the control systems and methods discussed above may provide a control system for unmanned aerial systems and/or a method for controlling unmanned aerial systems. Conventional unmanned aerial systems are controlled using control systems that require both hands of an operator to operate the control system. Using the control systems and/or the methods discussed above provide several benefits in controlling unmanned aerial systems, including intuitive single-handed, precise, non-cross-coupled motion within the airspace.

In another example, the control systems and methods discussed above may provide a control system for unmanned submersible systems and/or a method for controlling unmanned submersible systems. Conventional unmanned submersible systems are controlled using control systems that require both hands of an operator to operate the control system. Using the control systems and/or the methods discussed above provide several benefits in controlling unmanned submersible systems, including intuitive single-handed, precise, non-cross-coupled motion within the submersible space.

In another example, the control systems and methods discussed above may provide a control system for weapons targeting systems and/or a method for controlling weapons targeting systems. Conventional weapons targeting systems are controlled using control systems that require both hands of an operator to operate the control system. Using the control systems and/or the methods discussed above provide several benefits in controlling weapons targeting systems, including precise, intuitive, single-handed targeting.

In another example, the control systems and methods discussed above may provide a control system for counter-improvised-explosive-device (IED) systems and/or a method for controlling counter-IED systems. Conventional counter-IED systems are controlled using control systems that require both hands of an operator to operate the control system. Using the control systems and/or the methods discussed above provide several benefits in controlling counter-IED systems, including precise, intuitive, single-handed pointing or targeting.

In another example, the control systems and methods discussed above may provide a control system for heavy mechanized vehicles and/or a method for controlling heavy mechanized vehicles. Conventional heavy mechanized vehicles are controlled using control systems that require both hands of an operator to operate the control system. Using the control systems and/or the methods discussed above provide several benefits in controlling heavy mechanized vehicles, including precise, intuitive, single-handed targeting.

In another example, the control systems and methods discussed above may provide a control system for piloted aircraft (e.g., rotary wing aircraft) and/or a method for controlling piloted aircraft. Conventional piloted aircraft are controlled using control systems that require both hands of an operator to operate the control system. Using the control systems and/or the methods discussed above provide several benefits in controlling piloted aircraft, including precise, intuitive, single-handed, non-cross-coupled motion within the airspace for the piloted aircraft.

In another example, the control systems and methods discussed above may provide a control system for spacecraft rendezvous and docking and/or a method for controlling spacecraft rendezvous and docking. Conventional spacecraft rendezvous and docking is controlled using control systems that require both hands of an operator to operate the control system. Using the control systems and/or the methods discussed above provide several benefits in controlling spacecraft rendezvous and docking, including precise, intuitive, single-handed, non-cross-coupled motion within the space for rendezvous and/or docking.

In another example, the control systems and methods discussed above may provide a control system for air-to-air refueling (e.g., boom control) and/or a method for controlling air-to-air refueling. Conventional air-to-air refueling is controlled using control systems that require both hands of an operator to operate the control system. Using the control systems and/or the methods discussed above provide several benefits in controlling air-to-air refueling, including precise, intuitive, single-handed, non-cross-coupled motion within the airspace for refueling.

In another example, the control systems and methods discussed above may provide a control system for navigation in virtual environments (e.g., operational and simulated warfare) and/or a method for controlling navigation in virtual environments. Conventional navigation in virtual environments is controlled using control systems that require both hands of an operator to operate the control system. Using the control systems and/or the methods discussed above provide several benefits in controlling navigation in virtual environments, including precise, intuitive, single-handed, non-cross-coupled motion within the virtual environment.

In an embodiment, the control systems and methods discussed above may be utilized in a wide variety of industrial applications. While a number of industrial applications are discussed below, those examples are not meant to be limiting, and one of ordinary skill in the art will recognize that many other industrial applications may benefit from being able to provide rotational and translational movement using a single hand.

For example, the control systems and methods discussed above may provide a control system for oil exploration systems (e.g., drills, 3D visualization tools, etc.) and/or a method for controlling oil exploration systems. Conventional oil exploration systems are controlled using control systems that require both hands of an operator to operate the control system. Using the control systems and/or the methods discussed above provide several benefits in controlling oil exploration systems, including precise, intuitive, single-handed, non-cross-coupled motion within the formation.

In another example, the control systems and methods discussed above may provide a control system for overhead cranes and/or a method for controlling overhead cranes. Conventional overhead cranes are controlled using control systems that require both hands of an operator to operate the control system. Using the control systems and/or the methods discussed above provide a benefit in controlling overhead cranes where single axis motion is often limited, by speeding up the process and increasing accuracy.

In another example, the control systems and methods discussed above may provide a control system for cherry pickers or other mobile industrial lifts and/or a method for controlling cherry pickers or other mobile industrial lifts. Conventional cherry pickers or other mobile industrial lifts are often controlled using control systems that require both hands of an operator to operate the control system, and often allow translation (i.e., x, y, and/or z motion) in only one direction at a time. Using the control systems and/or the methods discussed above provide several benefits in controlling cherry pickers or other mobile industrial lifts, including simultaneous multi-axis motion via a single-handed controller.

In another example, the control systems and methods discussed above may provide a control system for firefighting systems (e.g., water cannons, ladder trucks, etc.) and/or a method for controlling firefighting systems. Conventional firefighting systems are often controlled using control systems that require both hands of an operator to operate the control system, and typically do not allow multi-axis reorientation and translation. Using the control systems and/or the methods discussed above provide several benefits in controlling firefighting systems, including simultaneous multi-axis motion via a single-handed controller.

In another example, the control systems and methods discussed above may provide a control system for nuclear material handling (e.g., gloveboxes, fuel rods in cores, etc.) and/or a method for controlling nuclear material handling. Conventional nuclear material handling systems are controlled using control systems that require both hands of an operator to operate the control system. Using the control systems and/or the methods discussed above provide several benefits in controlling nuclear material handling, including very precise, fluid, single-handed, multi-axis operations with sensitive materials.

In another example, the control systems and methods discussed above may provide a control system for steel manufacturing and other high temperature processes and/or a method for controlling steel manufacturing and other high temperature processes. Conventional steel manufacturing and other high temperature processes are controlled using control systems that require both hands of an operator to operate the control system. Using the control systems and/or the methods discussed above provide several benefits in controlling steel manufacturing and other high temperature processes, including very precise, fluid, single-handed, multi-axis operations with sensitive materials.

In another example, the control systems and methods discussed above may provide a control system for explosives handling (e.g., in mining applications) and/or a method for controlling explosives handling. Conventional explosives handling is controlled using control systems that require both hands of an operator to operate the control system. Using the control systems and/or the methods discussed above provide several benefits in controlling explosives handling, including very precise, fluid, single-handed, multi-axis operations with sensitive materials.

In another example, the control systems and methods discussed above may provide a control system for waste management systems and/or a method for controlling waste management systems. Conventional waste management systems are controlled using control systems that require both hands of an operator to operate the control system. Using the control systems and/or the methods discussed above provide several benefits in controlling waste management systems, including very precise, fluid, single-handed, multi-axis operations with sensitive materials.

In an embodiment, the control systems and methods discussed above may be utilized in a wide variety of consumer applications. While a number of consumer applications are discussed below, those examples are not meant to be limiting, and one of ordinary skill in the art will recognize that many other consumer applications may benefit from being able to provide rotational and translational movement using a single hand.

For example, the control systems and methods discussed above may provide a control system for consumer electronics devices e.g., Nintendo Wii® (Nintendo of America Inc., Redmond, Wash., USA), Nintendo DS®, Microsoft Xbox® (Microsoft Corp., Redmond, Wash., USA), Sony PlayStation® (Sony Computer Entertainment Inc., Corp., Tokyo, Japan), and other video consoles as may be known by one or more of ordinary skill in the art) and/or a method for controlling consumer electronics devices. Conventional consumer electronics devices are controlled using control systems that require both hands of an operator to operate the control system (e.g., a hand controller and keyboard, two hands on one controller, a Wii® "nunchuck" z-handed I/O device, etc.) Using the control systems and/or the methods discussed above provide several benefits in controlling consumer electronics devices, including the ability to navigate with precision through virtual space with fluidity, precision and speed via an intuitive, single-handed controller.

In another example, the control systems and methods discussed above may provide a control system for computer navigation in 3D and/or a method for controlling computer navigation in 3D. Conventional computer navigation in 3D is controlled using control systems that either require both hands of an operator to operate the control system or do not allow fluid multi-axis motion through space. Using the control systems and/or the methods discussed above provide several benefits in controlling computer navigation in 3D, including very precise, fluid, single-handed, multi-axis operations.

In another example, the control systems and methods discussed above may provide a control system for radio-controlled vehicles and/or a method for controlling radio-controlled vehicles. Conventional radio-controlled vehicles are controlled using control systems that require both hands of an operator to operate the control system. Using the control systems and/or the methods discussed above provide several benefits in controlling radio-controlled vehicles, including intuitive single-handed, precise, non-cross-coupled motion within the airspace for radio-controlled vehicles.

In another example, the control systems and methods discussed above may provide a control system for 3D computer aided drafting (CAD) image manipulation and/or a method for controlling 3D CAD image manipulation. Conventional 3D CAD image manipulation is controlled using control systems that either require both hands of an operator to operate the control system or do not allow fluid multi-axis motion through 3D space. Using the control systems and/or the methods discussed above provide several benefits in controlling 3D CAD image manipulation, including intuitive single-handed, precise, non-cross-coupled motion within the 3D space.

In another example, the control systems and methods discussed above may provide a control system for general aviation and/or a method for controlling general aviation. Conventional general aviation is controlled using control systems that require both hands and feet of an operator to operate the control system. Using the control systems and/or the methods discussed above provide several benefits in controlling general aviation, including intuitive single-handed, precise, non-cross-coupled motion within the airspace for general aviation.

It is understood that variations may be made in the above without departing from the scope of the invention. While specific embodiments have been shown and described, modifications can be made by one skilled in the art without departing from the spirit or teaching of this invention. The embodiments as described are exemplary only and are not limiting. Many variations and modifications are possible and are within the scope of the invention. Furthermore, one or more elements of the exemplary embodiments may be omitted, combined with, or substituted for, in whole or in part, with one or more elements of one or more of the other exemplary embodiments. Accordingly, the scope of protection is not limited to the embodiments described, but is only limited by the claims that follow, the scope of which shall include all equivalents of the subject matter of the claims.

What is claimed is:

1. A controller, comprising:
   a control member coupled to a gimbal and movable in at least three degrees of freedom relative to a base of the gimbal,
   the gimbal including a socket extending from the base and a ball mounted within the socket such that the ball can rotate within the socket in the three degrees of freedom,
   the gimbal including three detents and three energy storage members, with each detent extending from the socket and being biased against the ball in response to a force provided by an energy storage member from the three energy storage members,
   the ball defining a groove that is engaged with the three detents when the control member is in a null position, such that movement of the control member in at least one of three degrees of freedom from the null position disengages at least one detent from the groove, thereby providing tactile feedback to a user at the control member.

2. The controller of claim 1, wherein the three energy storage members are springs.

3. The controller of claim 1, wherein the three energy storage members, absent external forces applied to the control member, are configured to place the control member in the null position.

4. The controller of claim 1, further comprising a cap extending over an outer surface of the socket, with a coupler extending from the cap and coupled to the control member, the coupler further coupled to the ball such that angular displacement of the coupler causes corresponding rotation of the ball within the socket.

5. The controller of claim 4, wherein the coupler is a post with a first end coupled to the control member and a second end coupled within a complementary opening defined by the ball such that angular displacement of the post relative to the base causes rotation of the ball relative to the base.

6. The controller of claim 1, further comprising a sensor configured to detect angular displacement of the ball within the socket.

7. The controller of claim 6, wherein the sensor is disposed below the ball.

8. The controller of claim 1, wherein the control member is a first control member that is shaped for gripping by a user's hand, the controller further comprising a second control member mounted on the first control member in a location for displacement relative to the first control member by a digit on the user's hand while gripping the first control member.

9. The controller of claim 1, wherein the control member is configured to provide active mechanical feedback to the user indicative of displacement from null position in at least one degree of freedom.

10. The controller of claim 1, wherein the control member is configured to provide active feedback to the user indicative of displacement from null position in at least one degree of freedom, the active feedback including at least one of reactive motion, a force, vibration, or haptic.

11. A controller, comprising:
    a first control member mounted to a gimbal with a base, the gimbal including centering mechanisms to generate forces to inform a user of a null position by tactile feedback of the first control member relative to the base, the first control member movable relative to the base in three degrees of freedom; and
    a second control member mounted on the first control member in a position configured to be displaced by a digit of the user relative to the first control member, the second control member including centering mechanisms to generate forces to inform the user by tactile feedback of a null position of the second control member relative to the first control member.

12. The controller of claim 11, wherein the gimbal includes a socket and a ball movably coupled within the socket,
    the centering mechanisms being springs, the springs being engaged with detents of the socket to provide a force towards the ball and urge the first control member into the null position.

13. The controller of claim 12, wherein the detents include three pairs of detents, at least two pairs of which are orthogonally oriented relative to one another.

14. The controller of claim 11, further comprising a sensor configured to detect angular displacement of the first control member relative to the base.

15. The controller of claim 11, further comprising a magnet disposed below the ball and a Hall effector sensor disposed below the magnet, when the first control member is in the null position.

16. The controller of claim 11, wherein the first control member is configured to provide active mechanical feedback to the user indicative of displacement from null position in at least one degree of freedom.

\* \* \* \* \*